(12) United States Patent
Ohashi et al.

(10) Patent No.: US 11,010,375 B2
(45) Date of Patent: **\*May 18, 2021**

(54) INFORMATION PROCESSING UNIT, INFORMATION PROCESSING METHOD, AND PROGRAM

(71) Applicants: SONY CORPORATION, Tokyo (JP); JAPANESE FOUNDATION FOR CANCER RESEARCH, Tokyo (JP)

(72) Inventors: Takeshi Ohashi, Kanagawa (JP); Jun Yokono, Tokyo (JP); Takuya Narihira, Tokyo (JP)

(73) Assignee: SONY CORPORATION, Tokyo (JP)

( * ) Notice: Subject to any disclaimer, the term of this patent is extended or adjusted under 35 U.S.C. 154(b) by 378 days.

This patent is subject to a terminal disclaimer.

(21) Appl. No.: 15/695,456

(22) Filed: Sep. 5, 2017

(65) Prior Publication Data

US 2018/0004806 A1    Jan. 4, 2018

Related U.S. Application Data

(63) Continuation of application No. 14/652,581, filed as application No. PCT/JP2013/082807 on Dec. 6, 2013, now Pat. No. 9,798,770.

(30) Foreign Application Priority Data

Dec. 26, 2012  (JP) .............................. JP2012-283035

(51) Int. Cl.
*G06F 16/245* (2019.01)
*G06K 9/62* (2006.01)
(Continued)

(52) U.S. Cl.
CPC ............ *G06F 16/245* (2019.01); *G06F 16/51* (2019.01); *G06F 16/532* (2019.01);
(Continued)

(58) Field of Classification Search
USPC ....................................................... 707/754
See application file for complete search history.

(56) References Cited

U.S. PATENT DOCUMENTS 6,904,163 B1    6/2005 Fujimura et al.
7,713,204 B2 *  5/2010 Sakaguchi .............. G06T 5/002
                                                    600/441
(Continued)

FOREIGN PATENT DOCUMENTS

| JP | 2004-005364 | 1/2004 |
| JP | 2007-286945 | 11/2007 |
| JP | 2012-059251 | 3/2012 |

OTHER PUBLICATIONS

Mar. 23, 2018, Chinese Office Action issued for related CN application No. 201380067324.0.

(Continued)

*Primary Examiner* — Cam Linh T Nguyen
(74) *Attorney, Agent, or Firm* — Paratus Law Group, PLLC

(57) ABSTRACT

An information processing unit includes: a diagnostic image input section that inputs the diagnostic image; an operation information obtaining section that obtains display operation history information representing an operation history of a user who controls displaying of the diagnostic image; a query image generation section that extracts a predetermined region of the input diagnostic image to generate a query image; a diagnosed image obtaining section that supplies the generated query image and the display operation history information to a diagnosed image search unit and obtains the diagnosed image obtained as a search result by the diagnosed image search unit; and a display control section that displays the diagnostic image and the obtained diagnosed image for comparison.

44 Claims, 22 Drawing Sheets

(51) Int. Cl.
*G06F 16/51* (2019.01)
*G06F 16/58* (2019.01)
*G06F 16/532* (2019.01)
*G06F 16/583* (2019.01)
*G06T 7/00* (2017.01)
*G06K 9/00* (2006.01)
*G06F 16/535* (2019.01)
*G16H 30/20* (2018.01)

(52) U.S. Cl.
CPC ............ *G06F 16/535* (2019.01); *G06F 16/58* (2019.01); *G06F 16/583* (2019.01); *G06F 16/5866* (2019.01); *G06K 9/00147* (2013.01); *G06K 9/6215* (2013.01); *G06K 9/6253* (2013.01); *G06T 7/0012* (2013.01); *G16H 30/20* (2018.01); *G06T 2200/24* (2013.01); *G06T 2207/30024* (2013.01); *G06T 2207/30096* (2013.01)

(56) References Cited

U.S. PATENT DOCUMENTS

| | | | | | |
|---|---|---|---|---|---|
| 8,090,172 | B2* | 1/2012 | Shinagawa | ............ | G06T 11/003 382/128 |
| 8,165,362 | B2* | 4/2012 | Ishii | .............. | A61B 5/055 382/128 |
| 8,218,835 | B2* | 7/2012 | Matsuda | ............ | G16H 30/40 382/128 |
| 8,392,053 | B2* | 3/2013 | Gilbert | ............ | G16H 40/63 701/29.1 |
| 8,542,249 | B2* | 9/2013 | Ishida | ............ | G16H 30/40 345/629 |
| 8,611,988 | B2* | 12/2013 | Miyamoto | ............ | A61B 6/032 600/424 |
| 8,799,013 | B2* | 8/2014 | Gustafson | ............ | A61B 5/7264 705/2 |
| 9,342,744 | B2* | 5/2016 | Asa | ............ | G06K 9/00221 |
| 2002/0019751 | A1 | 2/2002 | Rothschild et al. | | |
| 2003/0013951 | A1 | 1/2003 | Stefanescu et al. | | |
| 2005/0078857 | A1* | 4/2005 | Park | ............ | A61B 5/0002 382/128 |
| 2005/0238216 | A1* | 10/2005 | Yoden | ............ | G06T 7/0012 382/128 |
| 2008/0075348 | A1 | 3/2008 | Rappaport et al. | | |
| 2008/0243395 | A1 | 10/2008 | Oosawa et al. | | |
| 2009/0080734 | A1 | 3/2009 | Moriya et al. | | |
| 2010/0076921 | A1 | 3/2010 | Kato et al. | | |
| 2010/0226550 | A1 | 9/2010 | Miyasa et al. | | |
| 2011/0075901 | A1* | 3/2011 | Nakamura | ............ | G06F 19/321 382/128 |
| 2011/0122138 | A1 | 5/2011 | Schmidt et al. | | |
| 2011/0238676 | A1* | 9/2011 | Liu | ............ | H04M 1/72555 707/752 |
| 2012/0063663 | A1 | 3/2012 | Kawasaki | | |
| 2012/0134550 | A1 | 5/2012 | Francois et al. | | |
| 2012/0327211 | A1 | 12/2012 | Yamamoto | | |
| 2013/0057547 | A1* | 3/2013 | Hwang | ............ | G06T 17/00 345/420 |
| 2013/0108133 | A1* | 5/2013 | Inoue | ............ | G06T 3/0037 382/131 |
| 2013/0254187 | A1 | 9/2013 | Sugihara | | |
| 2015/0286896 | A1* | 10/2015 | Watanabe | ............ | G06F 16/5854 382/103 |

OTHER PUBLICATIONS

Aug. 5, 2016 EP communication issued for related EP application No. 13868702.5.

* cited by examiner

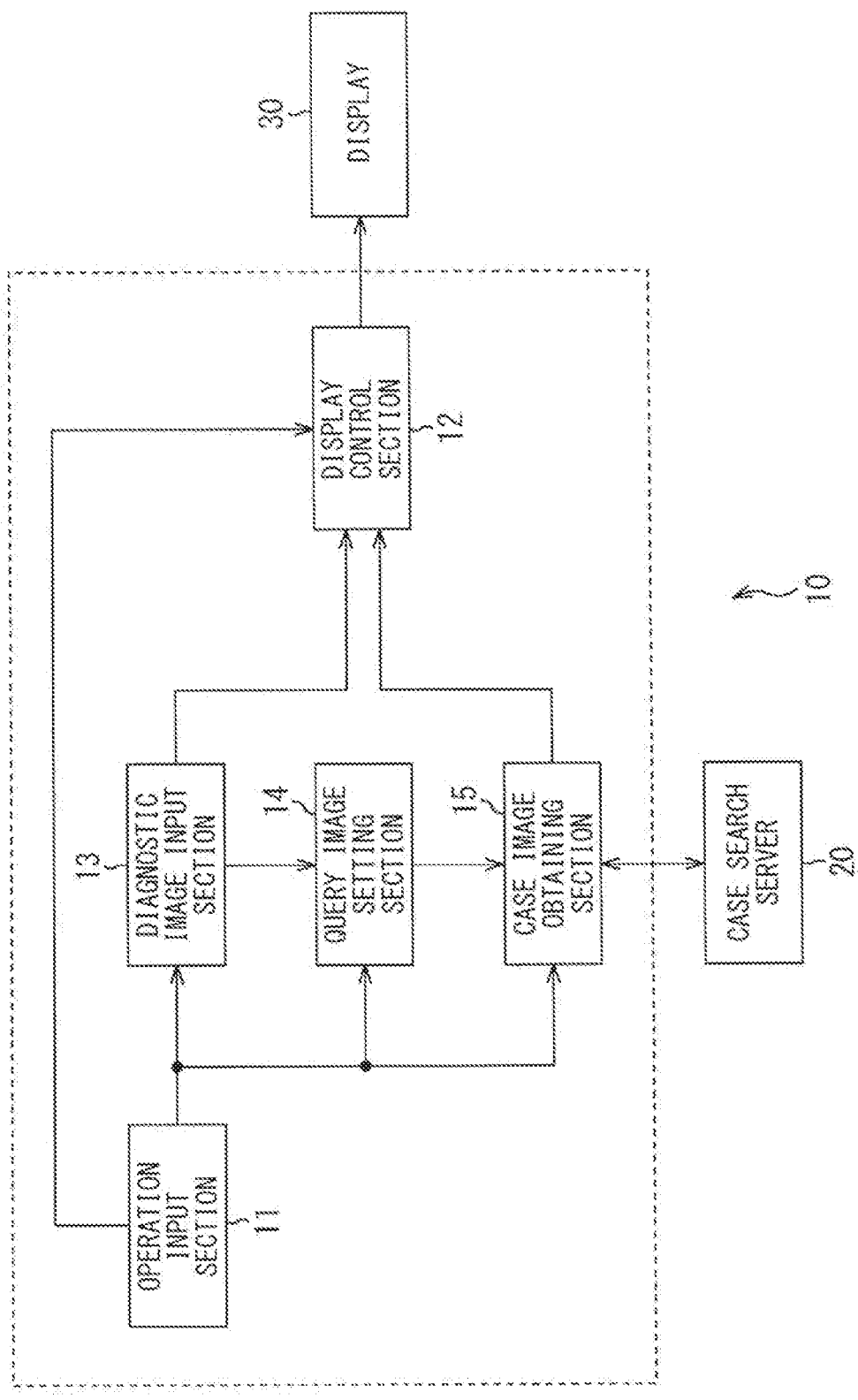

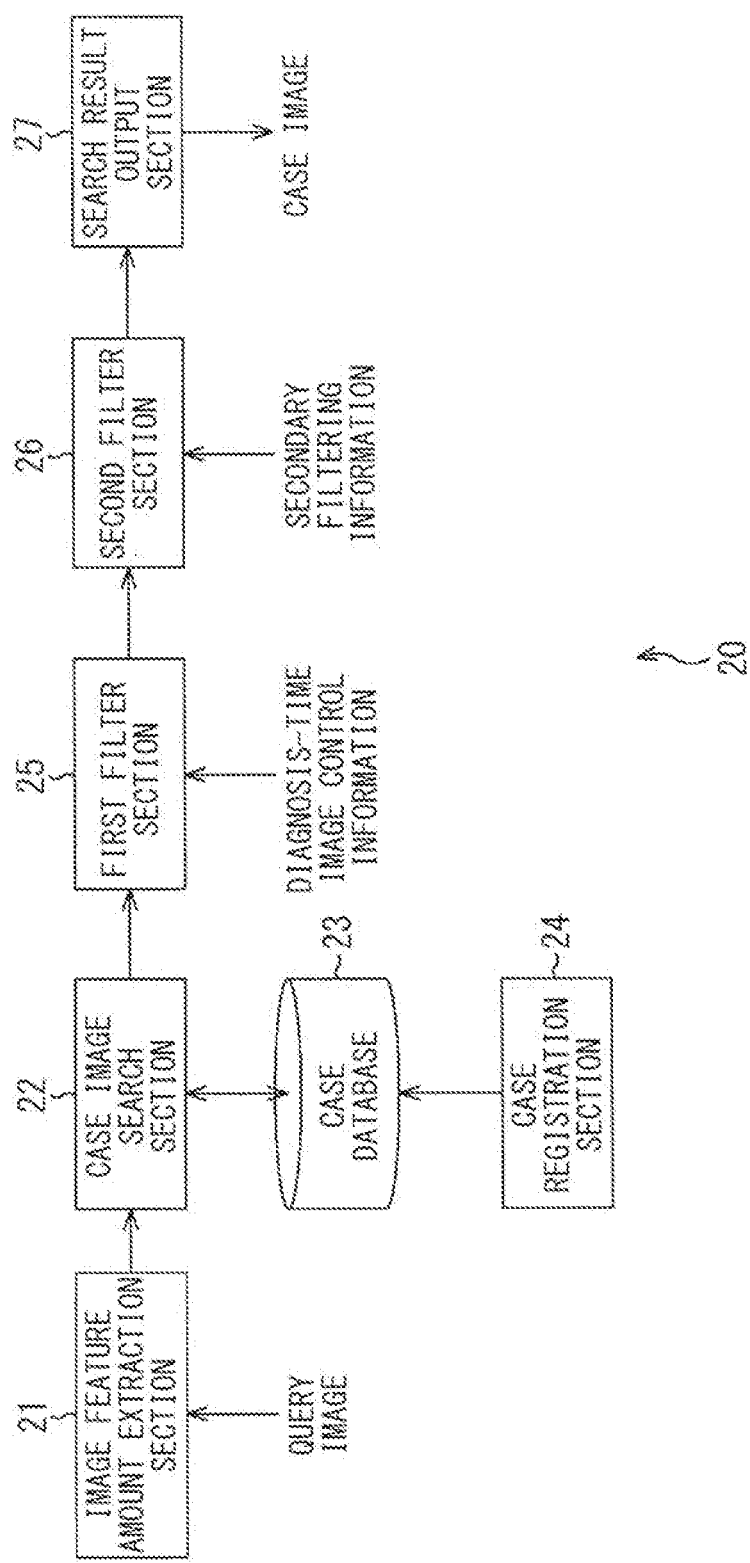
[FIG. 2]

[ FIG. 3 ]
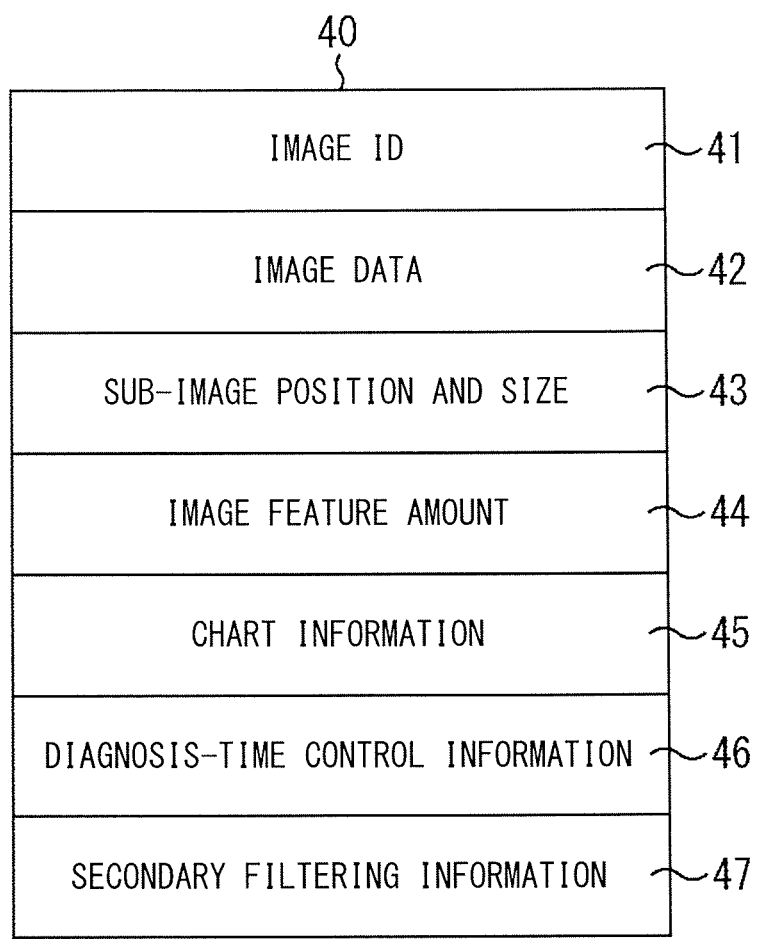

[FIG. 4]
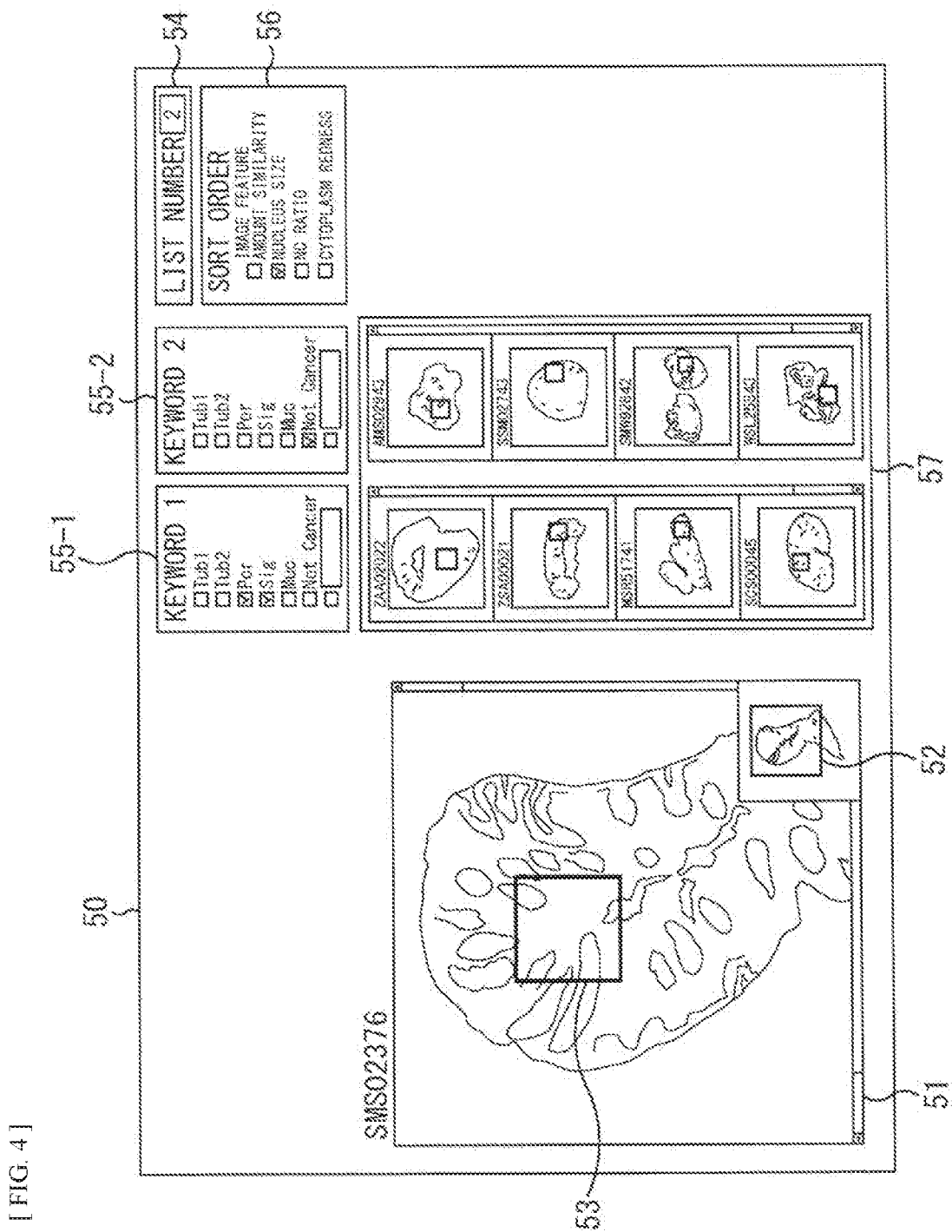

[ FIG. 5 ]
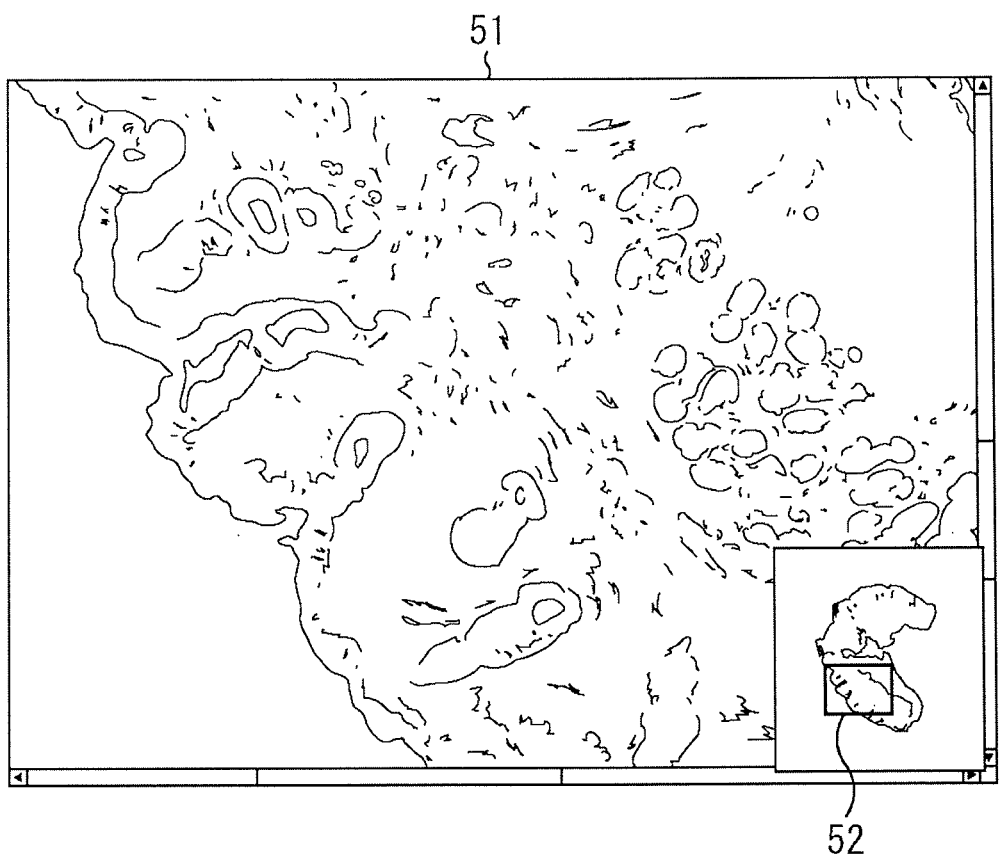

[ FIG.6 ]

DIAGNOSIS-TIME IMAGE CONTROL INFORMATION

| TIME | X COORDI-NATE | Y COORDI-NATE | DISPLAY MAGNIFI-CATION |
|---|---|---|---|
| t1 | 330 | 456 | 10 |
| t2 | 330 | 456 | 10 |
| t3 | 442 | 563 | 20 |
| t4 | 442 | 563 | 40 |
| ⋮ | | | |

[ FIG. 7 ]
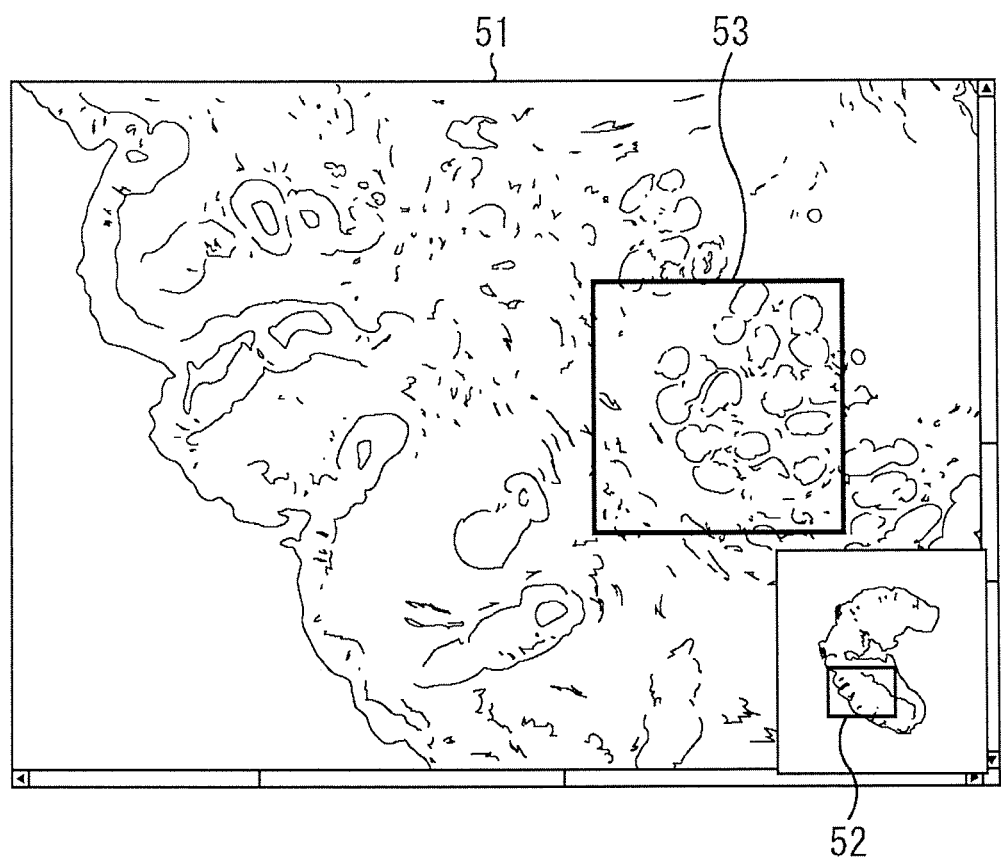

[FIG. 8]
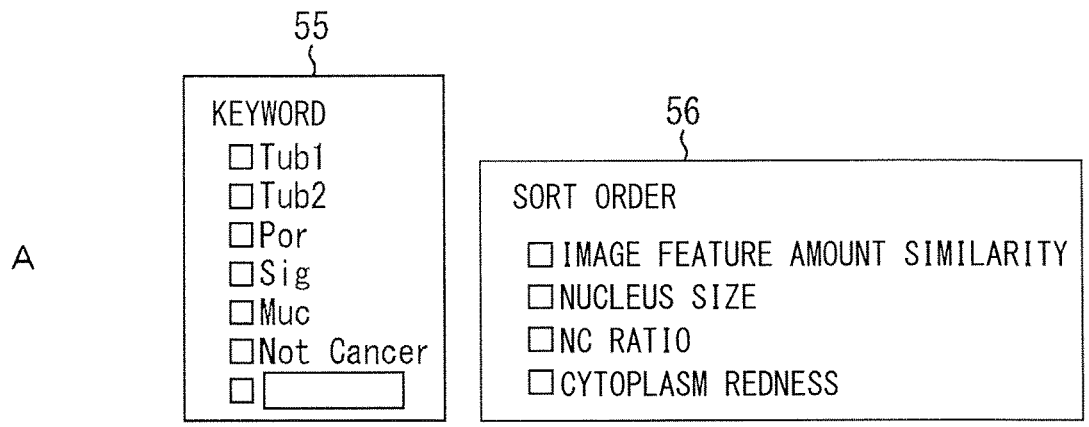
PATHOLOGY DIAGNOSIS OF STOMACH
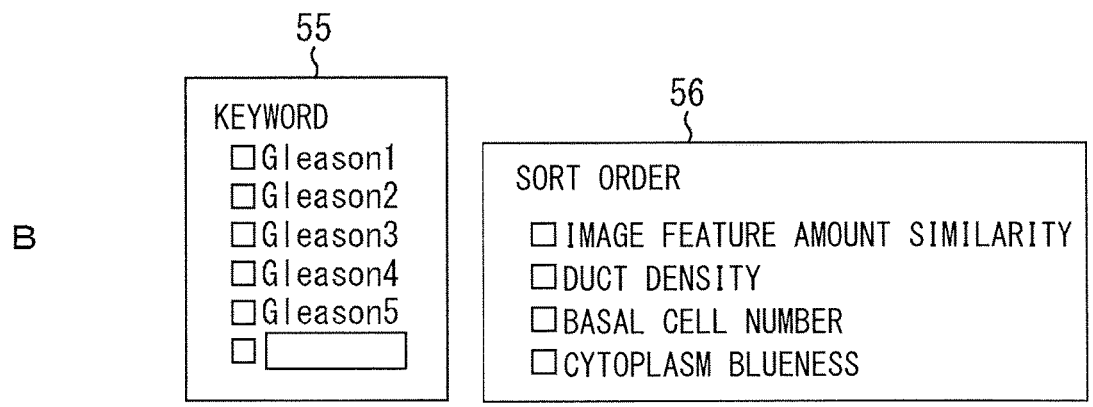
PATHOLOGY DIAGNOSIS OF PROSTATE GLAND

[ FIG. 9 ]
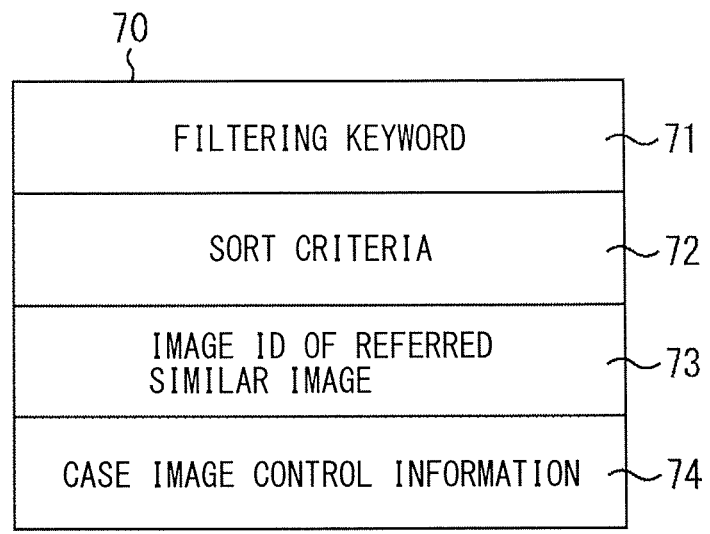

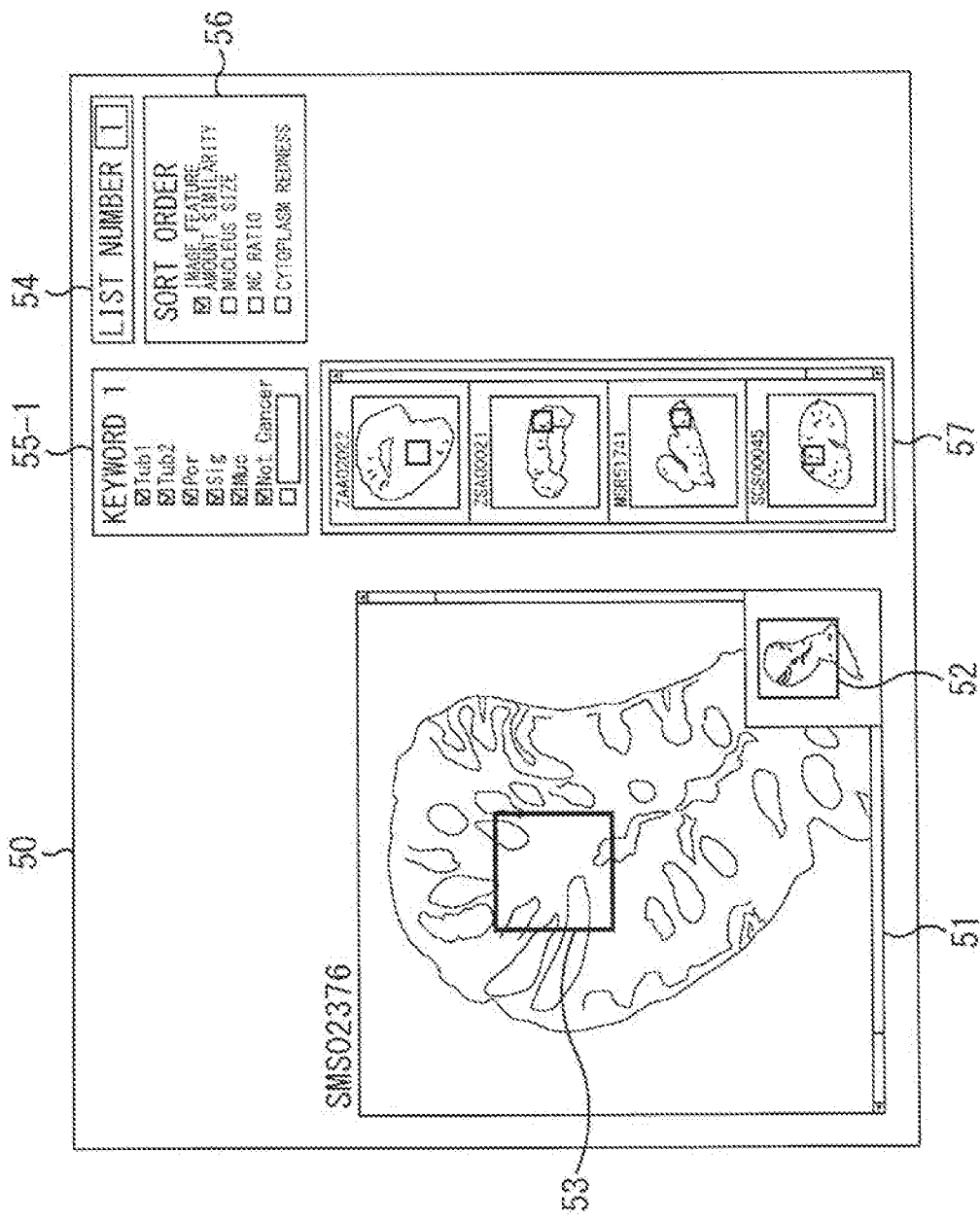

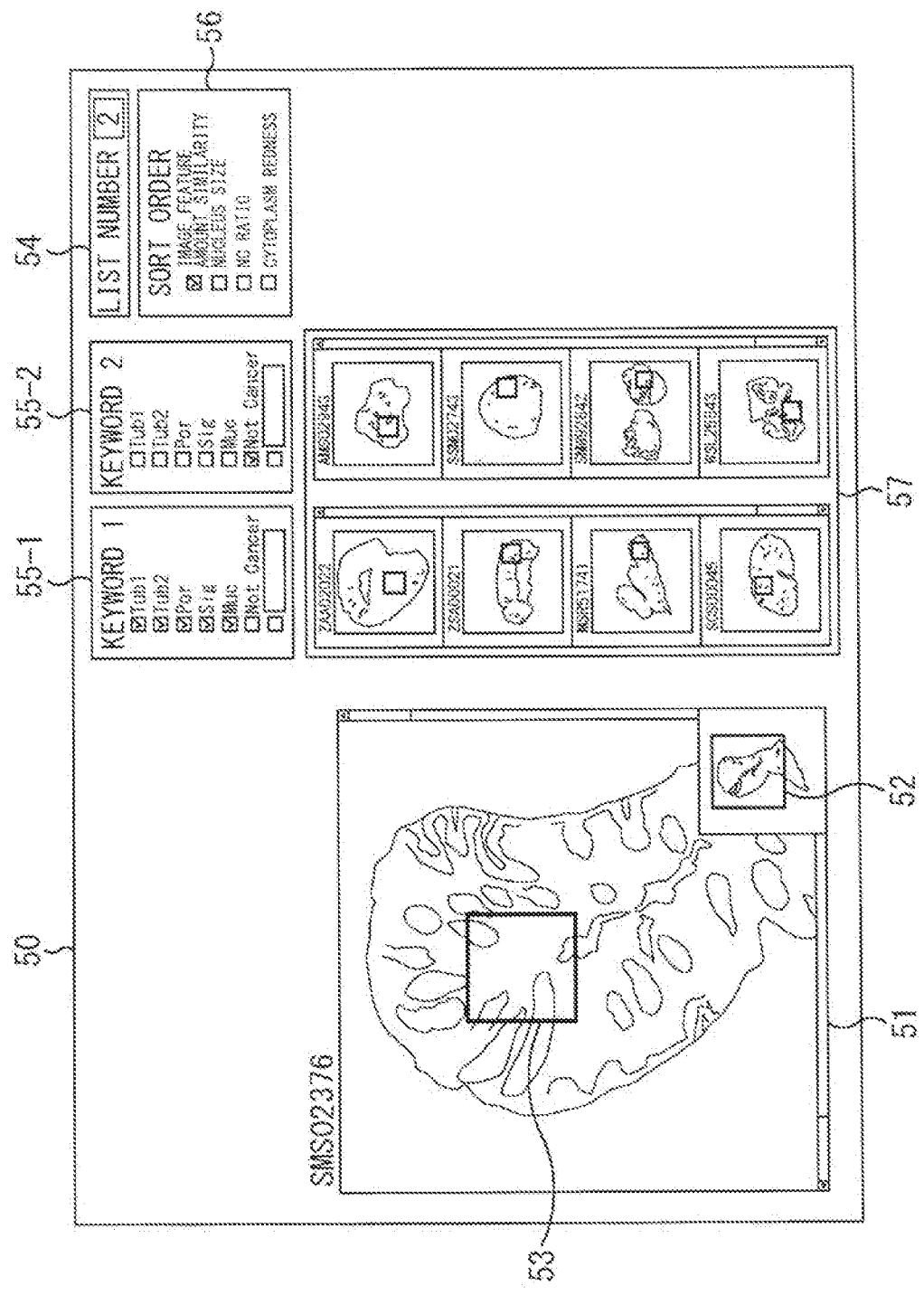

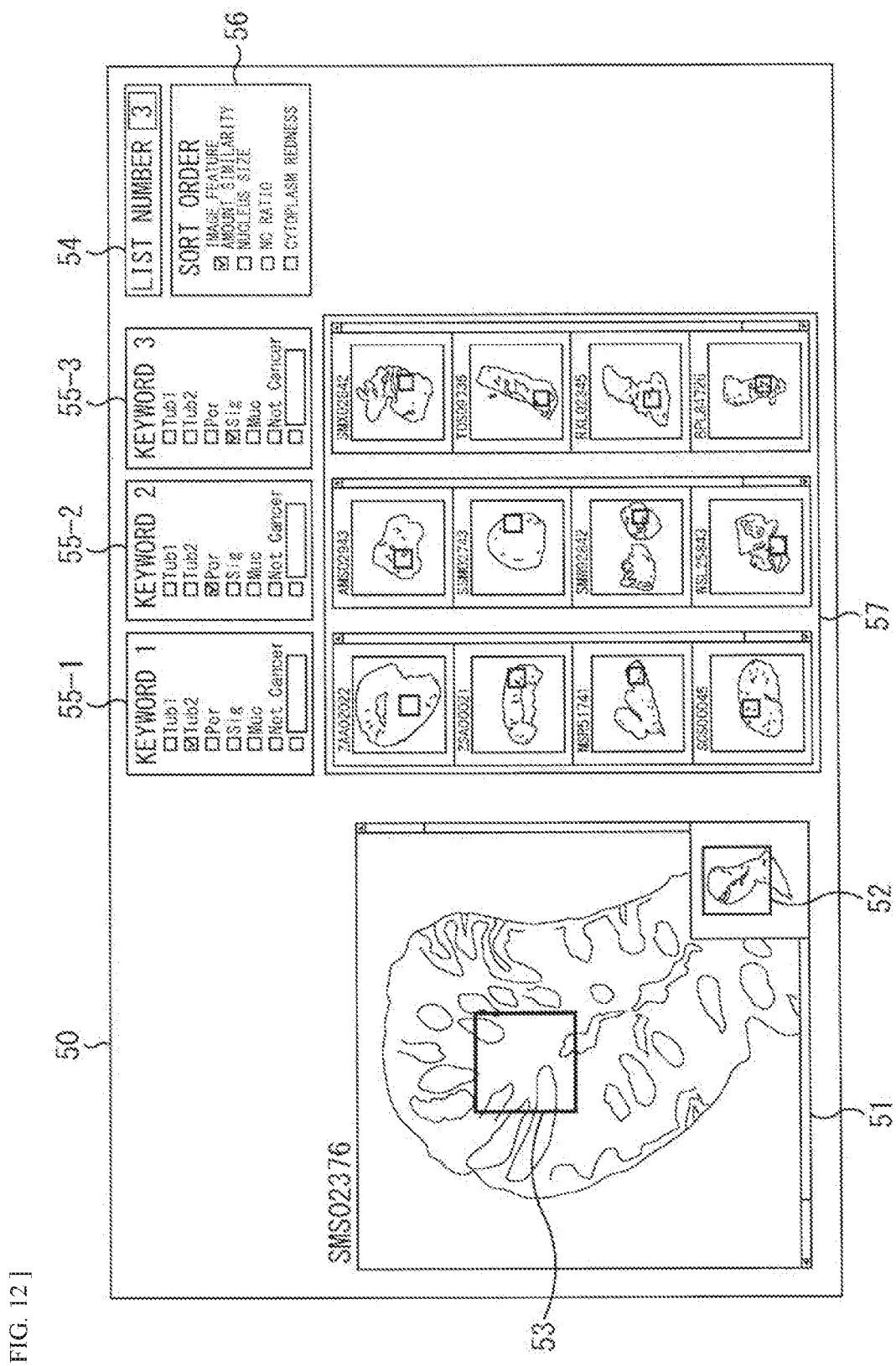
[FIG. 12]

[ FIG. 13 ]
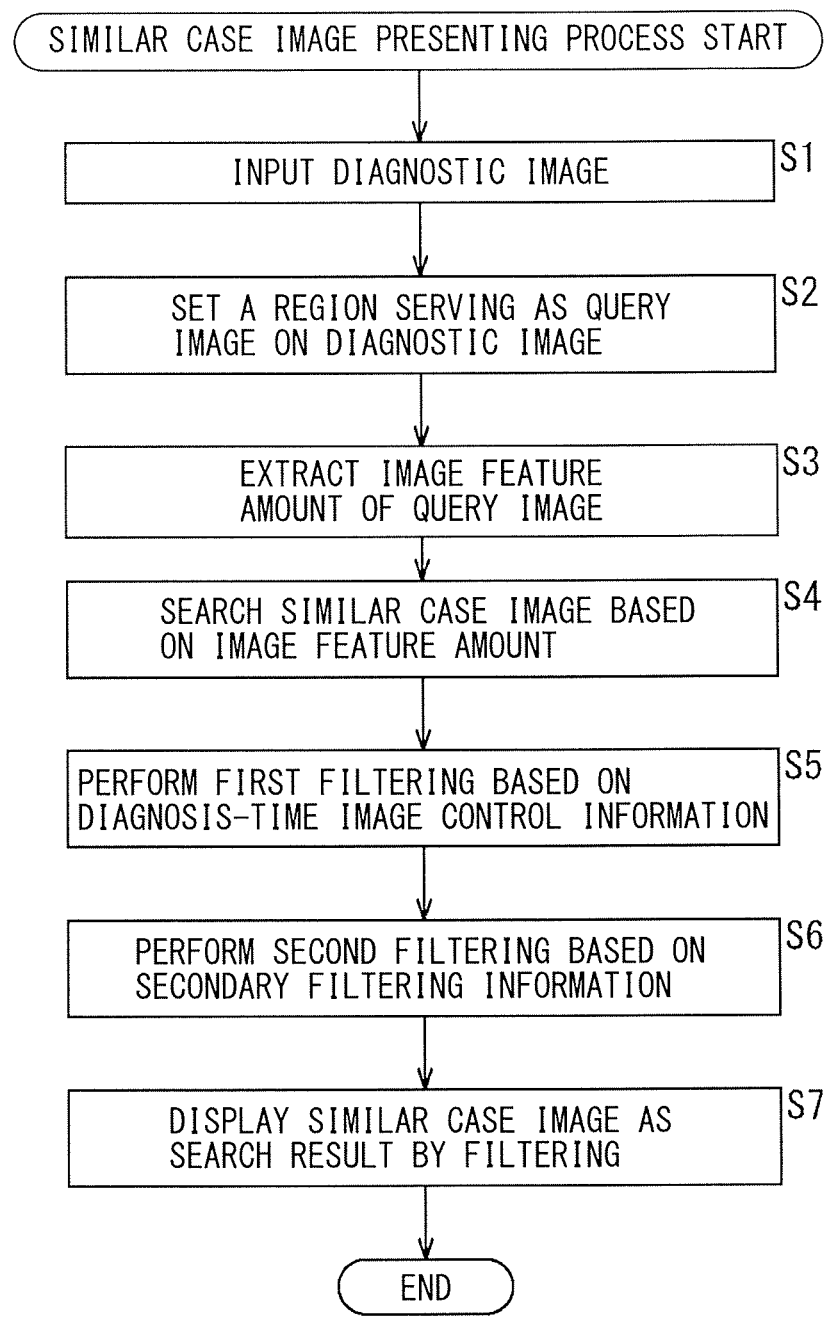

[FIG. 14]
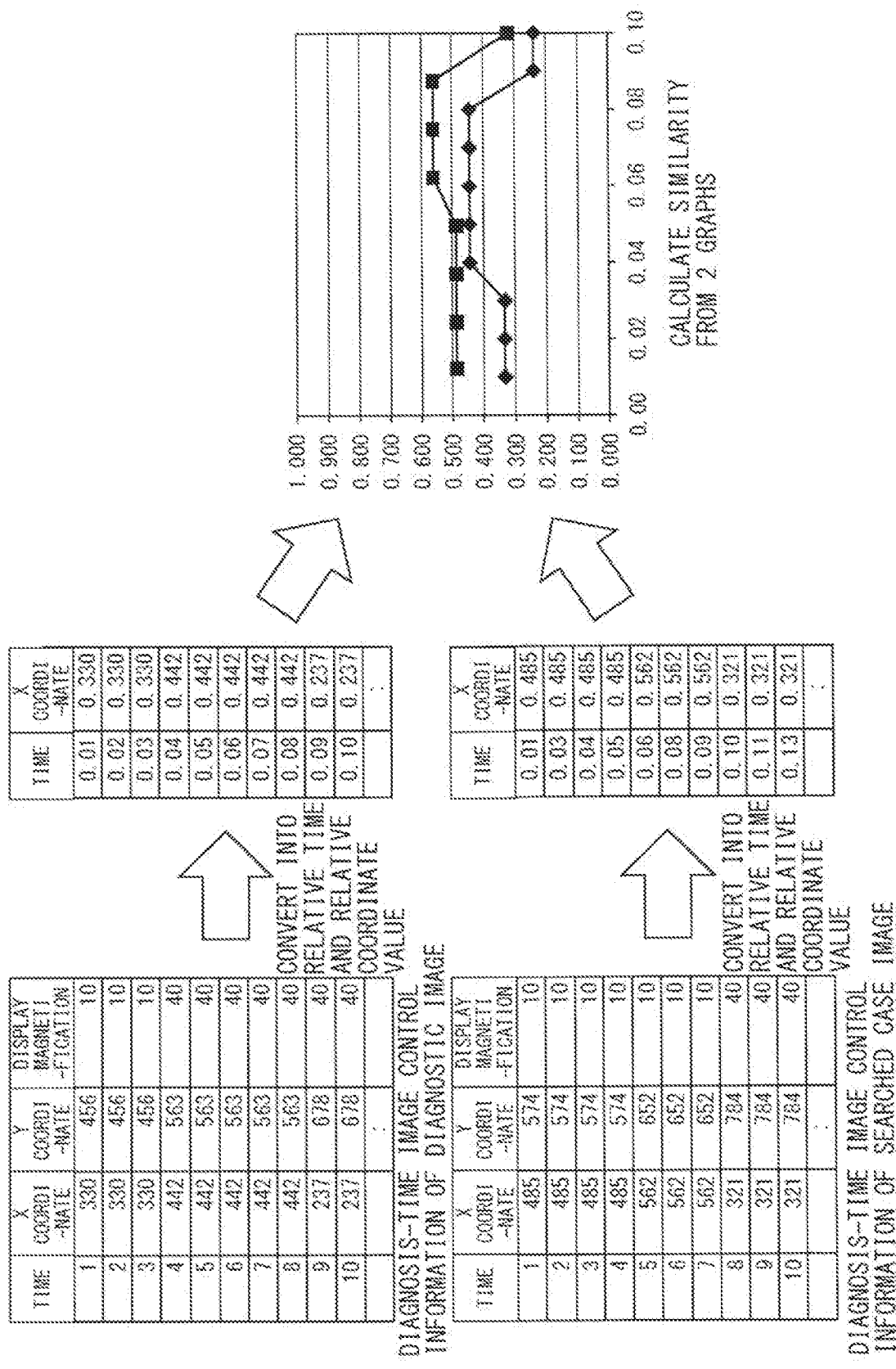

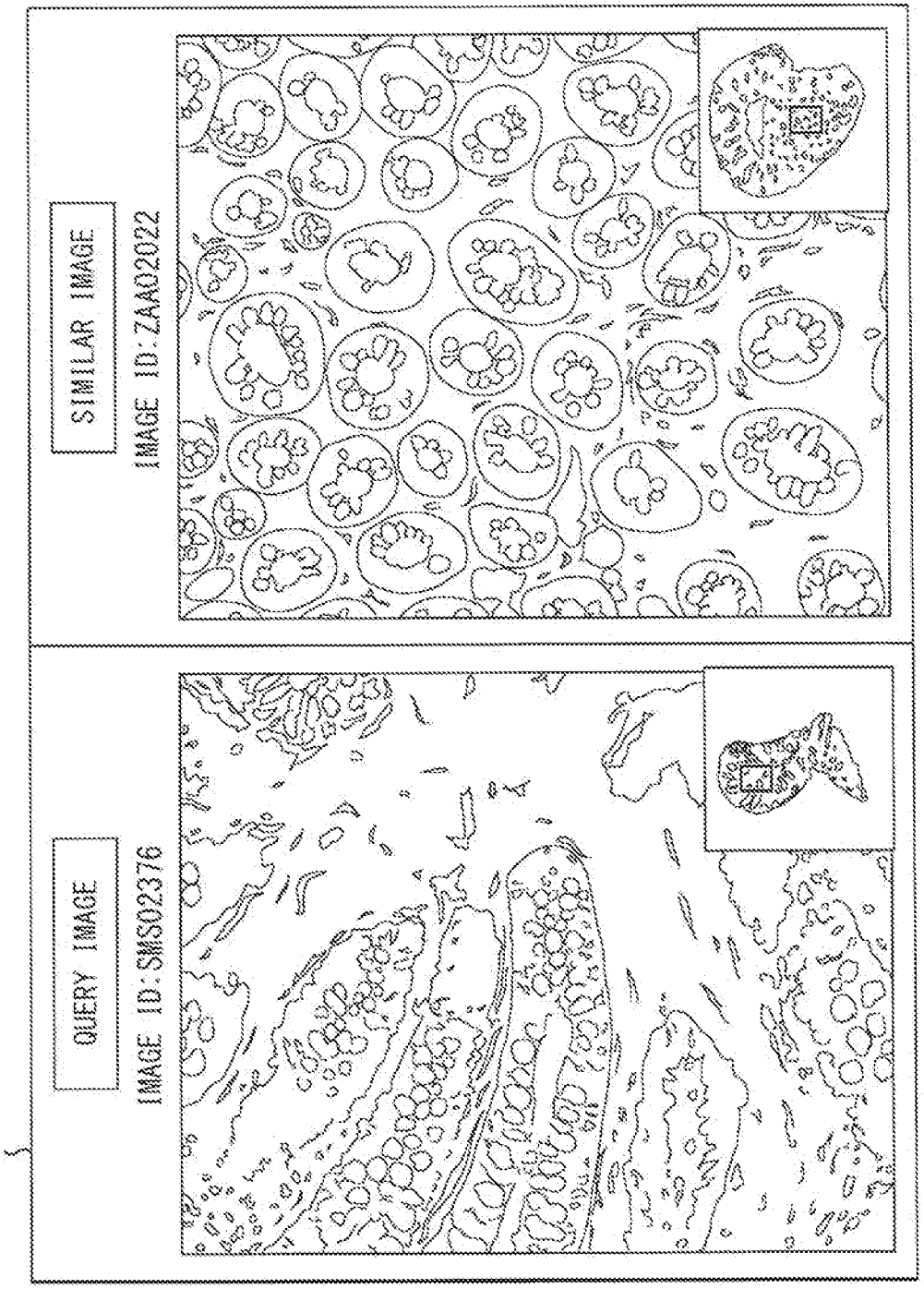
[FIG. 15]

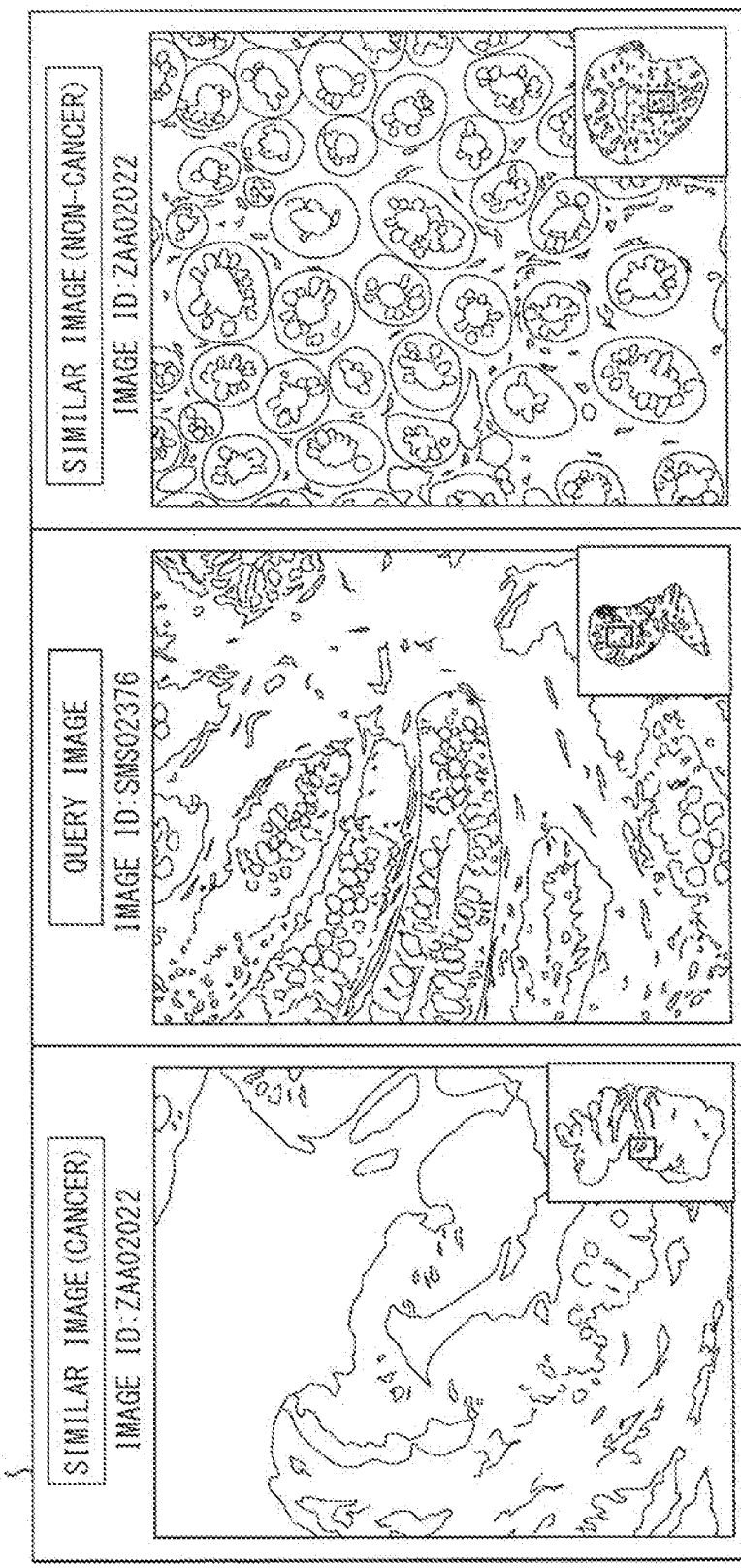
[FIG. 16]

[FIG. 17]
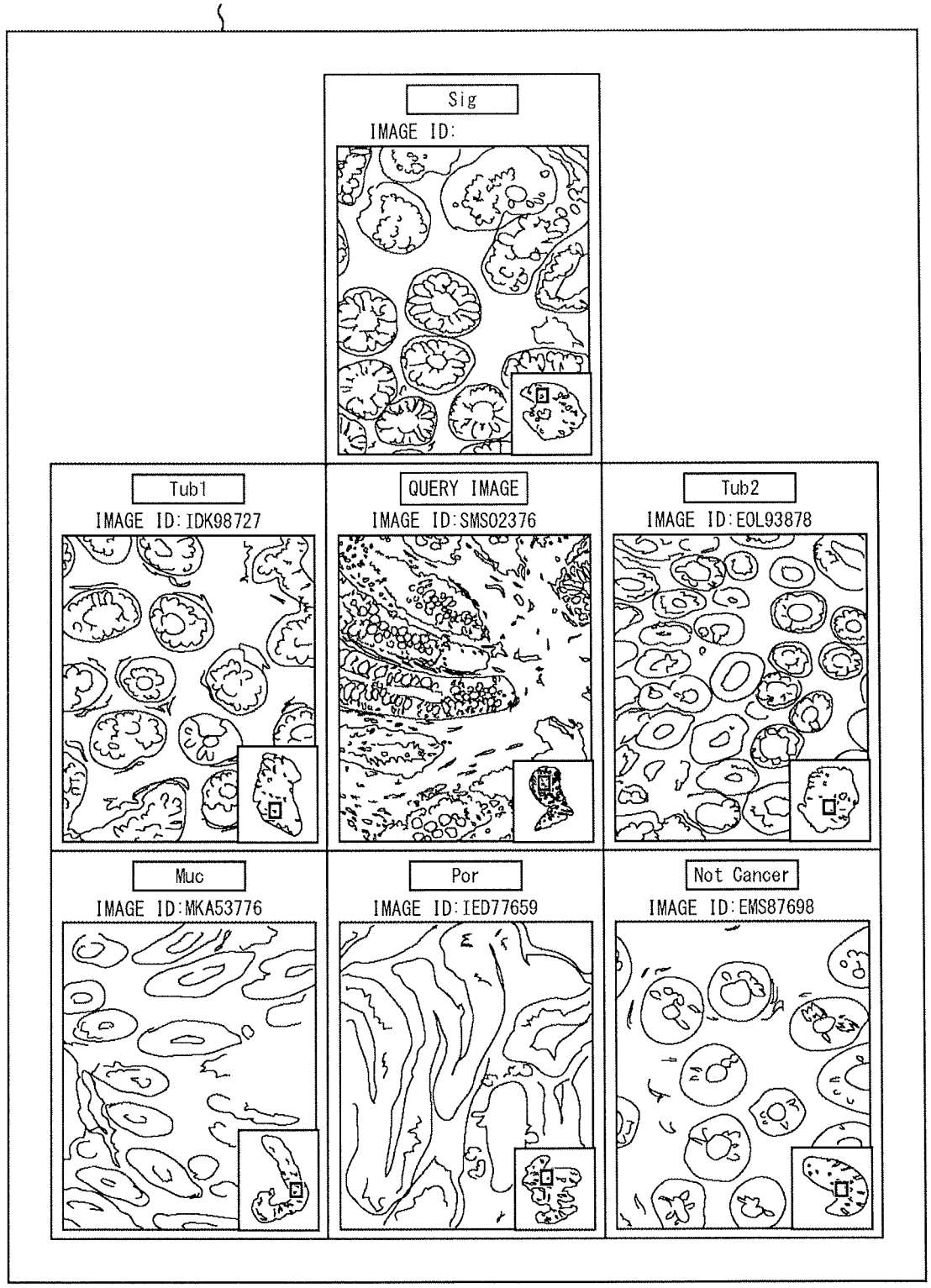

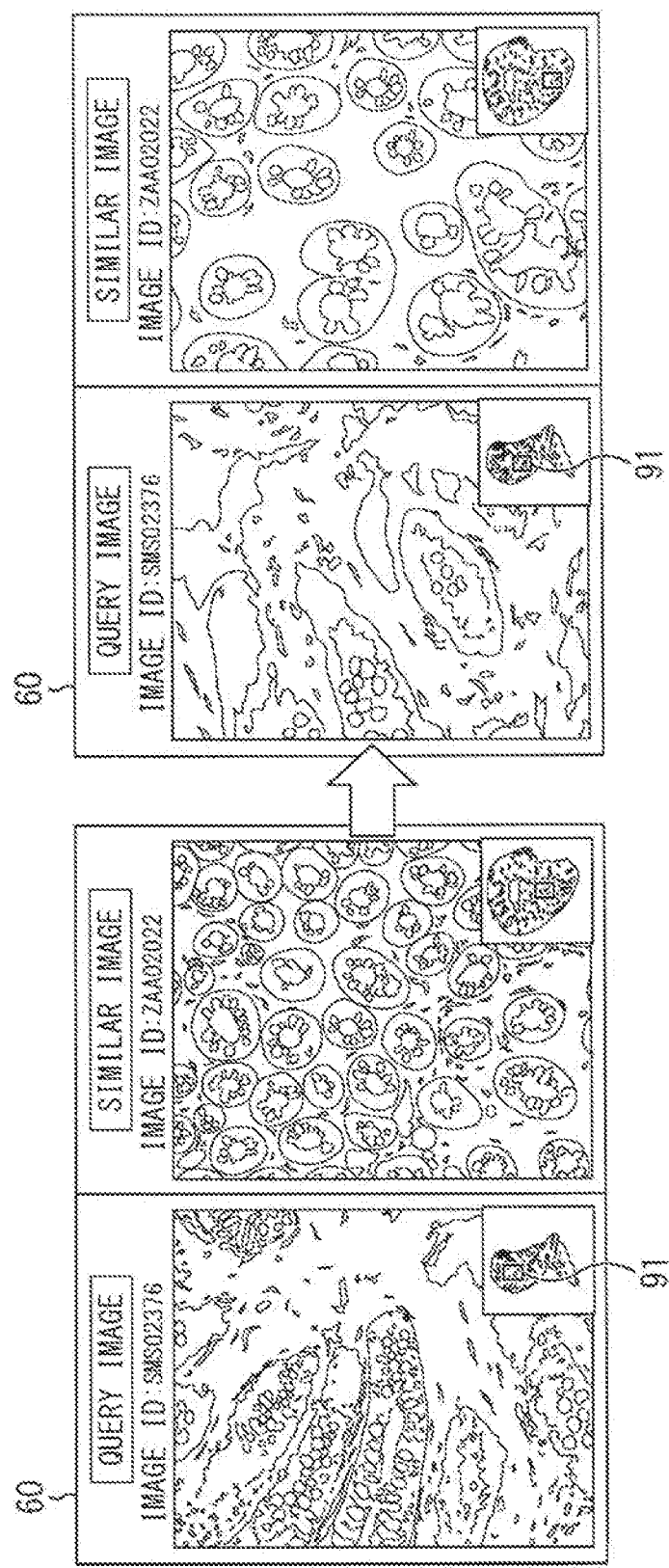

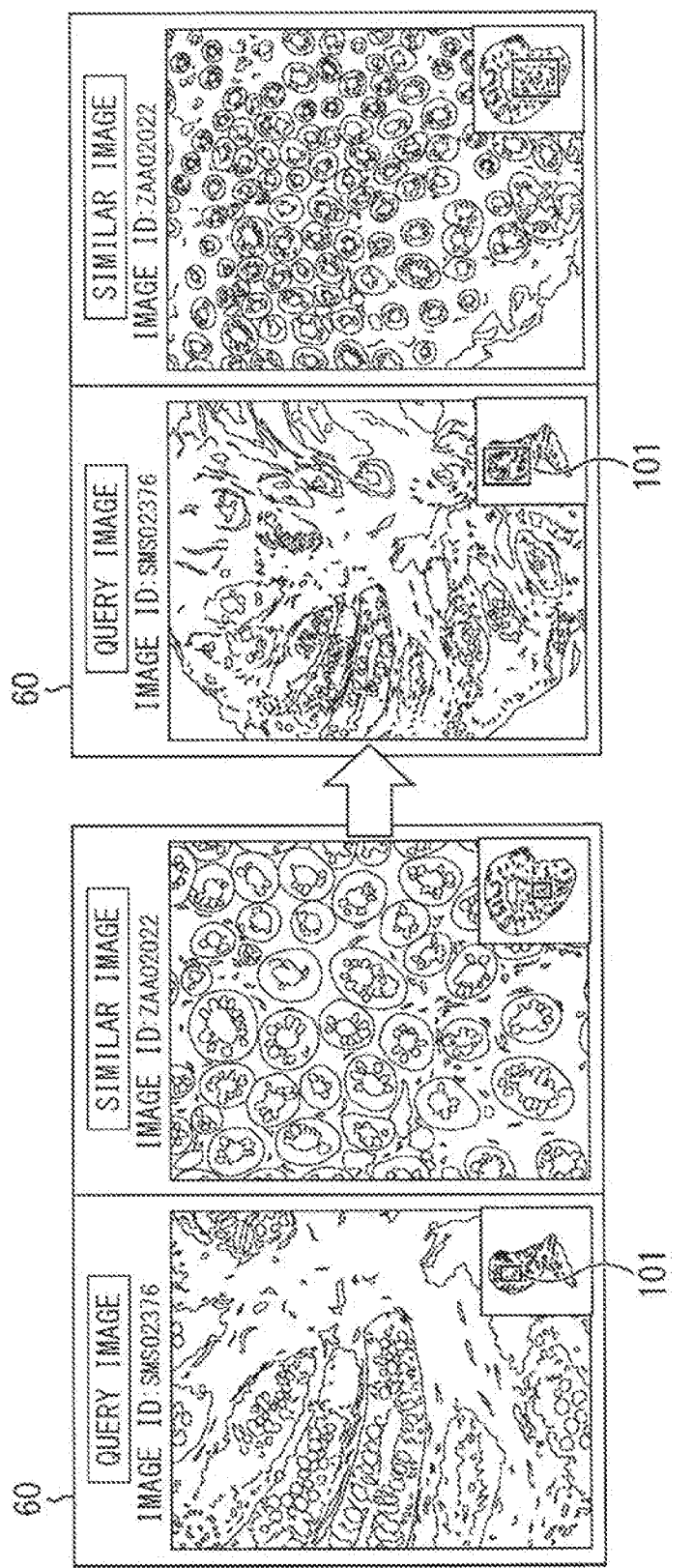

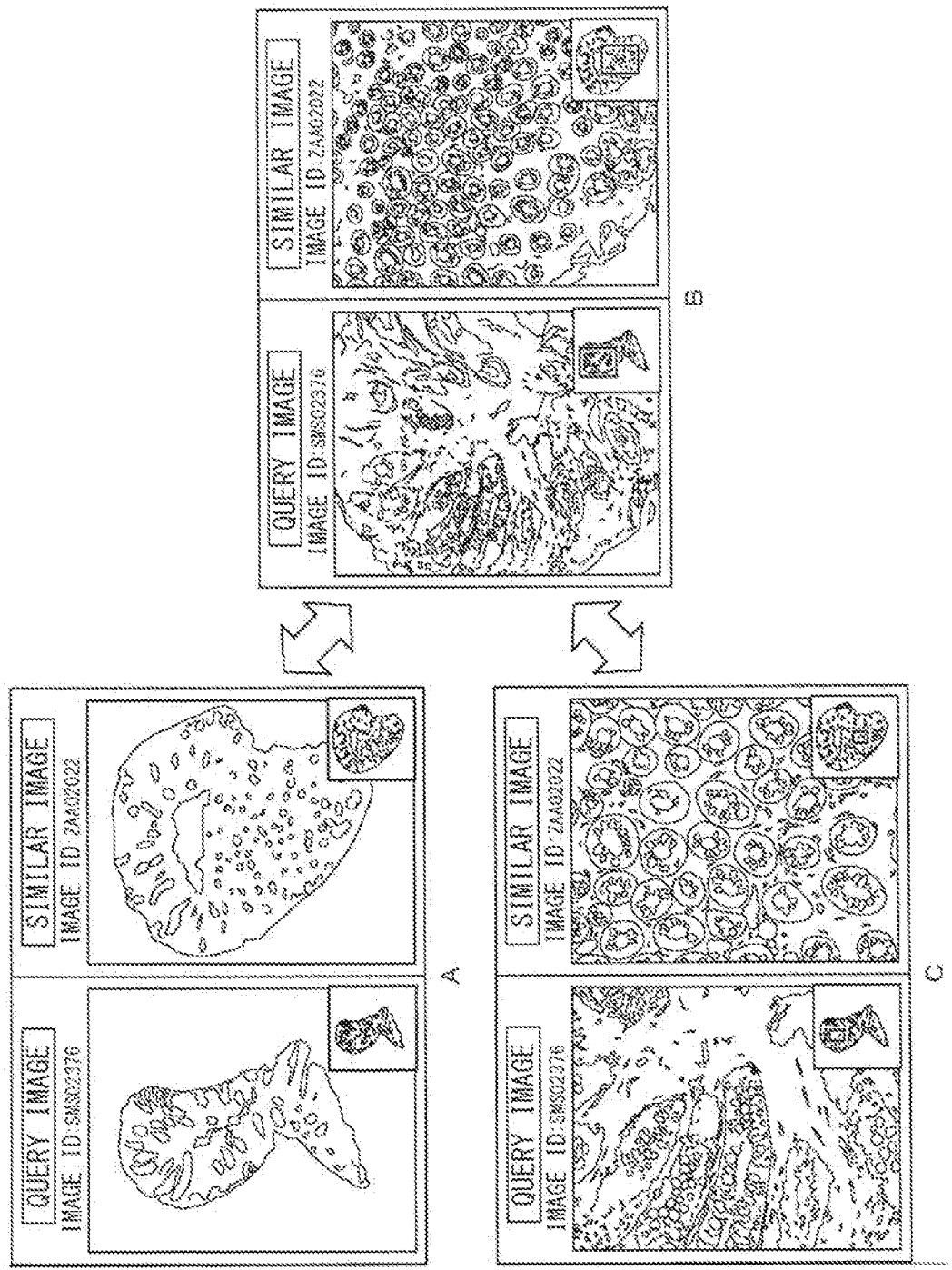
[FIG. 20]

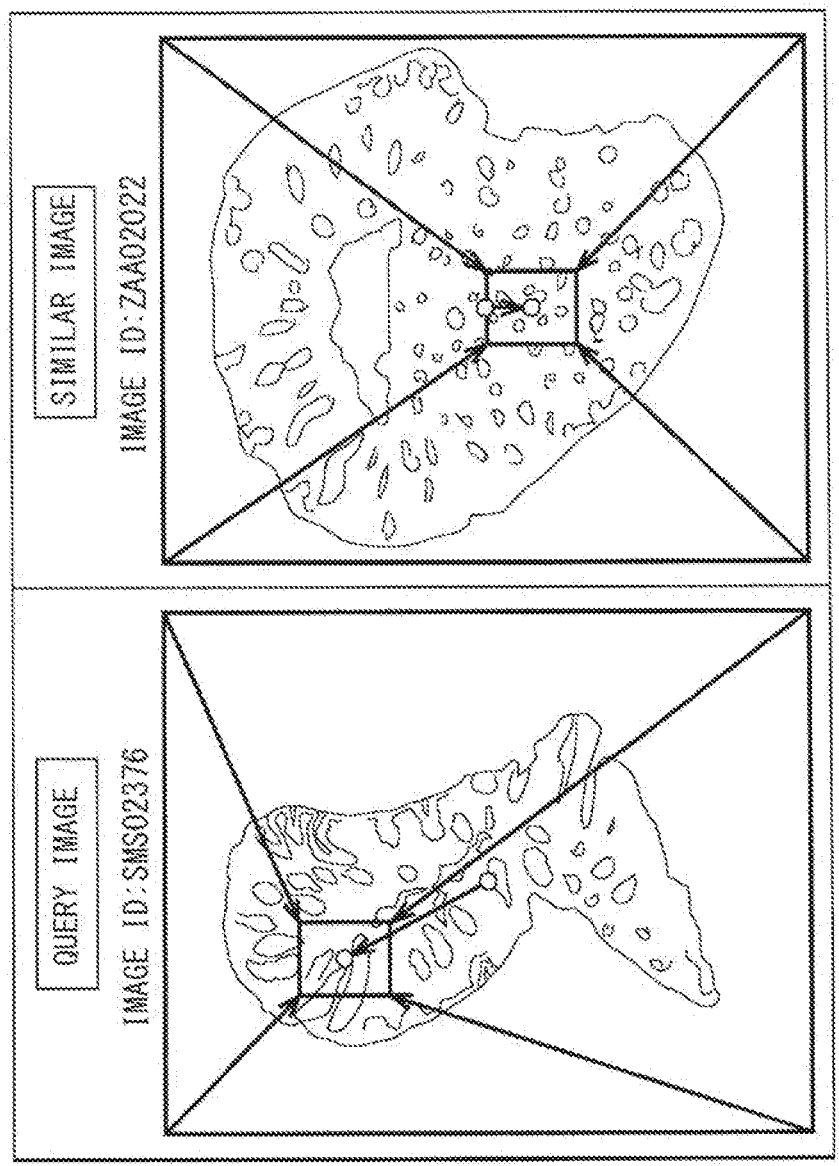
[FIG. 21]

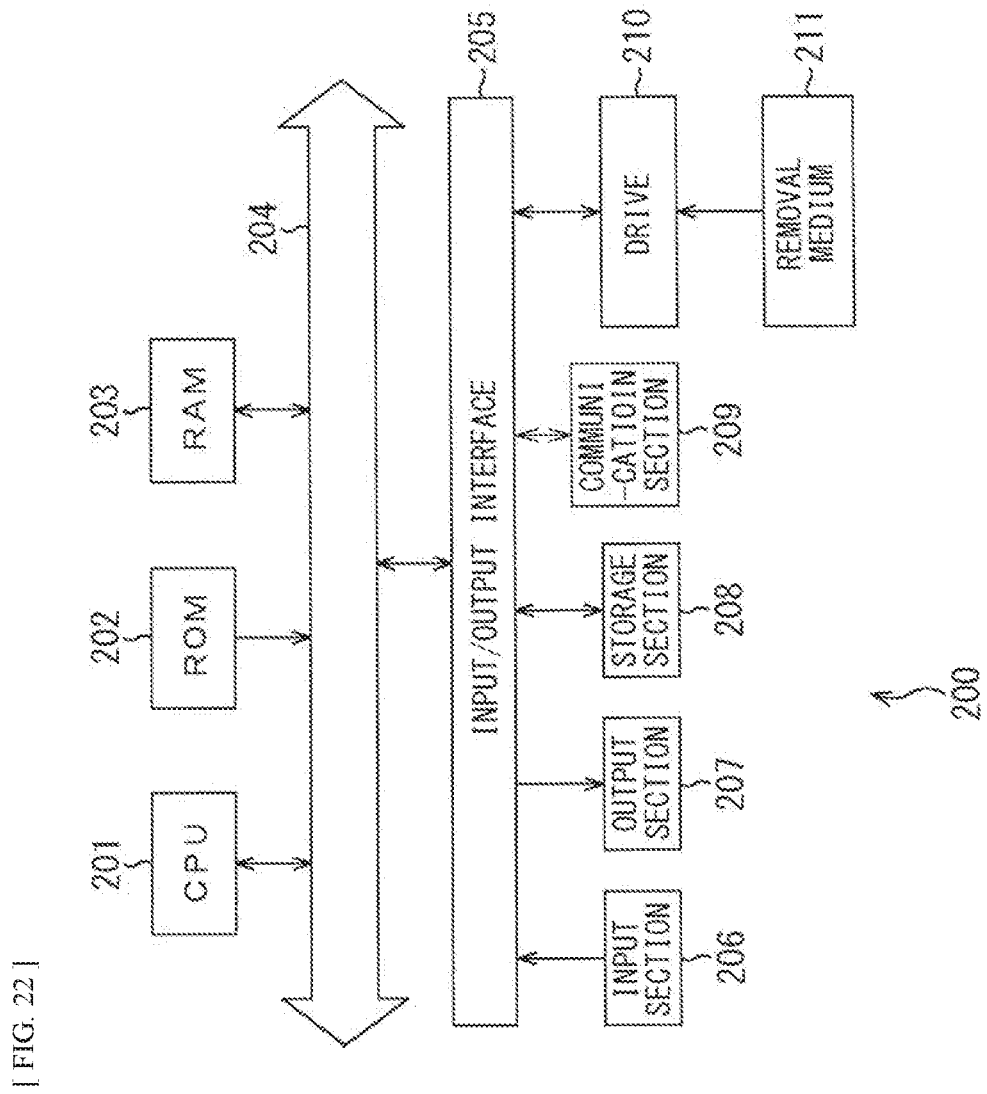
[FIG. 22]

INFORMATION PROCESSING UNIT, INFORMATION PROCESSING METHOD, AND PROGRAM

CROSS-REFERENCE TO PRIOR APPLICATION

This application is a continuation of U.S. patent application Ser. No. 14/652,581 (filed on Jun. 16, 2015), which is a National Stage patent application of PCT International Application No. PCT/JP2013/082807 (filed on Dec. 6, 2013) under U.S.C. § 371, which claims priority to Japanese Patent Application No. 2012-283035 (filed on Dec. 26, 2012), which are all hereby incorporated by reference in their entirety.

TECHNICAL FIELD

The present disclosure relates to an information processing unit, an information processing method, and a program, and specifically relates to an information processing unit, an information processing method, and a program that are suitable for, for example, use in a case where a case image similar to a diagnostic image as a diagnostic target is retrieved from a database and displayed.

BACKGROUND ART

In a medical setting, as a method of diagnosing a pathological tissue such as a tumor (for example, determining whether or not a pathological tissue is a malignant tumor such as cancer), there is a method in which a prepared specimen is formed by collecting a piece of a pathological tissue from a patient, slicing the piece of the pathological tissue, placing, on a glass slide, a section (hereinafter referred to as "biopsy specimen") obtained by slicing, and staining the biopsy specimen, and the prepared specimen is observed and diagnosed by a microscope or the like.

Moreover, to help such a diagnosis, there has been proposed a method in which scanning is performed on the prepared specimen, and an image similar to a diagnostic image obtained by the scanning is retrieved from a database holding case images that have been diagnosed, and is presented (for example, refer to PTL 1).

CITATION LIST

Patent Literature

PTL 1: Japanese Unexamined Patent Application Publication No. 2004-005364

SUMMARY OF INVENTION

In a method described in PTL 1, an image feature amount of a diagnostic image is compared to image feature amounts of case images in a database, and a case image retrieved simply based on similarity between them is presented. Therefore, a case image serving as a reference to diagnosis may not be retrieved, and a large number of search results that do not serve as references may be output.

Therefore, it is desirable to allow for efficiently retrieving an image similar to an image as a diagnostic target.

An information processing unit that displays a diagnostic image serving as a diagnosis target and a diagnosed image similar to the diagnostic image for comparison, the information processing unit includes: a diagnostic image input section that inputs the diagnostic image; an operation information obtaining section that obtains display operation history information representing an operation history of a user who controls displaying of the diagnostic image; a query image generation section that extracts a predetermined region of the input diagnostic image to generate a query image; a diagnosed image obtaining section that supplies the generated query image and the display operation history information to a diagnosed image search unit and obtains the diagnosed image obtained as a search result by the diagnosed image search unit; and a display control section that displays the diagnostic image and the obtained diagnosed image for comparison, and the diagnosed image search unit includes an image feature amount extraction section that extracts an image feature amount of the query image, a search section that retrieves diagnosed images each of which includes a sub-image with an image feature amount similar to the image feature amount of the query image from diagnosed images registered in advance, and a primary filter section that extracts a diagnosed image with display operation history information similar to the display operation history information corresponding to the diagnostic image that is a base of the query image from the diagnosed images retrieved by the search section.

The information processing unit according to the embodiment of the present disclosure may further include a keyword setting section that sets a keyword, and the diagnosed image obtaining section may also supply the set keyword to the diagnosed image search unit, and the diagnosed image search unit may further include a secondary filter section that extracts a diagnosed image corresponding to the set keyword from diagnosed images extracted by the primary filter section.

The information processing unit according to the embodiment of the present disclosure may include a plurality of the keyword setting sections, and the display control section may display diagnosed images obtained by the respective keyword setting sections.

When the display control section displays the diagnostic image and the obtained diagnosed image for comparison, in response to an operation from a user to instruct movement or zooming in or out of one of the diagnostic image and the diagnosed image, the display control section may also move or zoom in or out the other of the diagnostic image and the diagnosed image.

The diagnostic image and the diagnosed image may be medical images.

The diagnostic image and the diagnosed image may be pathological images obtained by scanning a prepared specimen, the prepared specimen being formed by placing, on a glass slide, a biopsy specimen cut from a pathological tissue, and staining the biopsy specimen.

The diagnosed image search unit may be a server provided on the Internet.

The information processing unit may include one or more of the image feature amount extraction section, the search section, the primary filter section, and the secondary filter section included in the diagnosed image search unit.

The display control section may display, as the diagnosed images, a first case image associated with information that a predetermined lesion is present and a second case image associated with information that the lesion is not present.

The display control section may display, in association with the first case image, display information indicating that the lesion is present, and displays, in association with the second image, display information indicating that the lesion is not present.

An information processing method according to an embodiment of the present disclosure is an information processing method of an information processing unit that displays a diagnostic image serving as a diagnosis target and a diagnosed image similar to the diagnostic image for comparison, and in the information processing unit, the diagnostic image is input; display operation history information representing an operation history of a user who controls displaying of the diagnostic image is obtained; a predetermined region of the input diagnostic image is extracted to generate a query image; the generated query image and the display operation history information are supplied to a diagnosed image search unit and the diagnosed image obtained as a search result by the diagnosed image search unit is obtained; and the diagnostic image and the obtained diagnosed image are displayed for comparison. The diagnosed image search unit executes extracting an image feature amount of the query image, retrieving diagnosed images each of which includes a sub-image with an image feature amount similar to the image feature amount of the query image from diagnosed images registered in advance, and extracting a diagnosed image with display operation history information similar to the display operation history information corresponding to the diagnostic image that is a base of the query image from the retrieved diagnosed images.

A program according to an embodiment of the present disclosure allows a computer that displays a diagnostic image serving as a diagnosis target and a diagnosed image similar to the diagnostic image for comparison to function as: a diagnostic image input section that inputs the diagnostic image; an operation information obtaining section that obtains display operation history information representing an operation history of a user who controls displaying of the diagnostic image; a query image generation section that extracts a predetermined region of the input diagnostic image to generate a query image; a diagnosed image obtaining section that supplies the generated query image and the display operation history information to a diagnosed image search unit and obtains the diagnosed image obtained as a search result by the diagnosed image search unit; and a display control section that displays the diagnostic image and the obtained diagnosed image for comparison, and the diagnosed image search unit includes an image feature amount extraction section that extracts an image feature amount of the query image, a search section that retrieves diagnosed images each of which includes a sub-image with an image feature amount similar to the image feature amount of the query image from diagnosed images registered in advance, and a primary filter section that extracts a diagnosed image with display operation history information similar to the display operation history information corresponding to the diagnostic image that is a base of the query image from the diagnosed images retrieved by the search section.

In the embodiments of the present disclosure, the diagnostic image is input; the display operation history information representing the operation history of the user that controls displaying of the diagnostic image is obtained; and the predetermined region of the diagnostic image input is extracted to generate a query image. Moreover, the generated query image and the display operation history information are supplied to the diagnosed image search unit, the diagnosed image obtained as a search result by the diagnosed image search unit is obtained, and the diagnostic image and the obtained diagnosed image are displayed for comparison. It is to be noted that, in the diagnosed image search unit, the image feature amount of the query image is extracted, the diagnosed images each of which includes a sub-image with an image feature amount similar to the image feature amount of the query image are retrieved from diagnosed images registered in advance, and a diagnosed image with display operation history information similar to the display operation history information corresponding to the diagnostic image that is a base of the query image is extracted from the retrieved diagnosed images.

BRIEF DESCRIPTION OF DRAWINGS

FIG. 1 is a block diagram illustrating a configuration example of a similar case image presentation unit to which an embodiment of the present disclosure is applied.

FIG. 2 is a block diagram illustrating a configuration example of a case search server in FIG. 1.

FIG. 3 is a diagram illustrating items of case information.

FIG. 4 is a diagram illustrating a display example of a user interface of the similar case image presentation unit.

FIG. 5 is a diagram illustrating a display example of a diagnostic image display region.

FIG. 6 is a diagram illustrating an example of diagnosis-time image control information.

FIG. 7 is a diagram illustrating a display example of a query image set frame.

FIG. 8 is a diagram illustrating examples of keywords and sort criteria depending on a part that is to be diagnosed.

FIG. 9 is a diagram illustrating data items of secondary filtering information.

FIG. 10 is a diagram illustrating a display example of search results in a case where the list number is 1.

FIG. 11 is a diagram illustrating a display example of search results in a case where the list number is 2.

FIG. 12 is a diagram illustrating a display example of search results in a case where the list number is 3.

FIG. 13 is a flow chart describing a similar case image presenting process.

FIG. 14 is a diagram describing similarity calculation of diagnosis-time image control information.

FIG. 15 is a diagram illustrating a display example in a case where a query image and a similar image are compared to each other.

FIG. 16 is a diagram illustrating a display example in a case where a query image and similar images are compared to each other.

FIG. 17 is a diagram illustrating a display example in a case where a query image and similar images are compared to each other.

FIG. 18 is a display example in a case where a query image and a similar image are concurrently scrolled.

FIG. 19 is a display example in a case where a query image and a similar image are concurrently zoomed in.

FIG. 20 is a diagram for describing center movement in a case where a query image and a similar image are concurrently zoomed in or out.

FIG. 21 is a diagram illustrating center movement in the case where the query image and the similar image are concurrently zoomed in or out.

FIG. 22 is a block diagram illustrating a configuration example of a computer.

DESCRIPTION OF EMBODIMENTS

Some best modes for carrying out the present disclosure (hereinafter referred to as "embodiments") will be described in detail below referring to the accompanying drawings.

[Configuration Example of Similar Case Image Display Control Unit]

A similar case image display control unit as an embodiment of an information processing unit of the present disclosure is configured to present a diagnosed pathological image similar to a pathological image as a diagnostic target to a user (such as a pathologist) for comparison, when the pathological image as the diagnostic subject is observed.

As used herein, the term "pathological image" refers to an image obtained by scanning a prepared specimen (that is obtained by cutting a biopsy specimen from a body tissue, placing the biopsy specimen on a glass slide, and staining the biopsy specimen) that is generally observed by a diagnostician such as a pathologist under a microscope.

It is to be noted that the present disclosure is also applicable to a case where, in addition to the pathological image, a medical image obtained by picking up an image of a human body or the like by CT, MRI, X-rays, or the like, and an arbitrary image not limited to the medical field are presented.

Hereinafter, a pathological image obtained by scanning a prepared specimen as a diagnostic target is referred to as "diagnostic image". Moreover, a pathological image that has been diagnosed is referred to as "case image".

FIG. 1 illustrates a configuration example of the similar case image display control unit.

This similar case image presentation unit 10 is configured of an operation input section 11, a display control section 12, a diagnostic image input section 13, a query image setting section 14, and a case image obtaining section 15.

The operation input section 11 accepts a diagnostic image selection operation by the user (such as a pathologist serving as a diagnostician), operations of movement or zooming in/out of a displayed diagnostic image, a setting operation of a query image provided on the diagnostic image, an input operation of a search condition (such as a keyword), and the like. Moreover, the operation input section 11 inputs an operation signal according to an input operation to the display control section 12, the diagnostic image input section 13, the query image setting section 14, or the case image obtaining section 15 corresponding to the operation signal.

The display control section 12 displays a screen 50 (FIG. 4) serving as a user interface on a display 30 in a following stage. A diagnostic image, a case image displayed as a search result, and the like are displayed in the screen 50 serving as the user interface. It is to be noted that a specific display example of the screen 50 will be described later.

The diagnostic image input section 13 determines a diagnostic image serving as a diagnostic target from pathological images prepared in advance in response to an operation signal based on a selection operation by the user, and inputs the diagnostic image to the display control section 12 and the query image setting section 14.

The query image setting section 14 extracts, from the displayed diagnostic image, a region indicated by a query set frame 53 with a predetermined size set on the diagnostic image by the user, and inputs a resultant query image to the case image obtaining section 15.

The case image obtaining section 15 transmits the query image to a case search server 20 to request retrieval. At this time, the case image obtaining section 15 also supplies, to the case search server 20, diagnostic image control information that indicates an operation history of the user relating to displaying of the diagnostic image, and secondary filtering information (both of which will be described later). Then, the case image obtaining section 15 obtains a case image obtained as a search result of the case search server 20 to supply the case image to the display control section 12.

The case search server 20 may be provided on, for example, the Internet. However, the entire case search server 20 or some of constituent components of the case search server 20 may be built in the similar case image presentation unit 10.

FIG. 2 illustrates a configuration example of the case search server 20.

The case search server 20 is configured of an image feature amount extraction section 21, a case image search section 22, a case database 23, a case registration section 24, a first filter section 25, a second filter section 26, and a search result output section 27.

The image feature amount extraction section 21 extracts an image feature amount from the query image to supply the image feature amount to the case image search section 22. As a method of extracting the image feature amount, any existing method may be applied, as long as the method is in common with a method of extracting an image feature amount of a case image registered in the case database 23 that will be described below.

More specifically, for example, a frequency feature of a texture of the query image may be extracted by FFT, or a histogram feature amount of a luminance gradient such as HOG and SHIFT feature amounts may be extracted. The extracted image feature amount may be represented by, for example, an N-dimensional vector.

The case image search section 22 retrieves case images each of which includes a sub-image similar to the query image from the case database 23, based on the image feature amount of the query image, and inputs search results thus obtained (not only image data but also entire case information including the image data) to the first filter section 25. Hereinafter, the sub-image, as a search result, similar to the query image on the case image is also referred to as "similar image".

The case database 23 holds a large number of case images that has been diagnosed. It is to be noted that a sub-image representing a region that is marked in diagnosis and has the same size as that of the query image is provided on the case image, and case information per sub-image is registered in the case database 23. This sub-image on the case image may serve as a similar image in a following stage.

FIG. 3 illustrates items included in the case information.

The case information 40 corresponding to each sub-image includes an image ID 41, image data 42, sub-image position and size 43, an image feature amount 44, chart information 45, diagnosis-time image control information 46, and secondary filtering information 47.

The image ID 41 is identification information individually assigned to each of sub-images on case images. The image data 42 is image data representing each pixel value of the case image including the sub-image. The sub-image position and size 43 are information representing a position and a size of the sub-image in the case image. The image feature amount 44 is an image feature amount of the sub-image. It is to be noted that it is necessary to adopt a same method for an image feature amount extraction method to obtain the image feature amount 44 and an image feature amount extraction method of the image feature extraction section 21. The chart information 45 is a character string representing a diagnosis result that has been already obtained of the case image including the sub-image.

The diagnosis-time image control information 46 represents a display operation history of the user when the case image including the sub-image is diagnosed, and corresponds to diagnosis-time image control information 60 that will be described later. The secondary filtering information 47 is set by the user when the case image including the sub-image is diagnosed, and corresponds to secondary filtering information 70 that will be described later.

The case registration section 24 registers case information for each of sub-images on case images in the case database 23. It is to be noted that a diagnosis result of a diagnostic image diagnosed by the user with use of the similar case image presentation unit 10 may be registered in the case database 23.

The first filter section 25 performs primary filtering on the search results based on the image feature amount from the case image search section 22, based on the diagnosis-time image control information. As used herein, the diagnosis-time image control information refers to information representing an operation history when an operation of display control such as movement (scrolling from side to side and up and down) and zooming in/out of the diagnostic image when the user makes a diagnosis. The diagnosis-time image control information will be described later referring to FIG. 6.

The second filter section 26 performs secondary filtering on primary filtering results by the first filter section 25, based on secondary filtering information. Herein, the secondary filtering information is configured of items such as a keyword and sort criteria that are input by the user to narrow the primary filtering results. The secondary filtering information will be described later referring to FIG. 9.

The search result output section 27 outputs results (case images each of which includes a region serving as a similar image) of the secondary filtering by the second filter section 26 to the case image obtaining section 15 of the similar case image presentation unit 10.

[About Screen Serving as User Interface]

Next, FIG. 4 illustrates a display example of a screen serving as a user interface.

This display screen 50 is displayed on the display 30, based on control by the display control section 12. A diagnostic image display region 51, a list number setting region 54, a keyword input region 55, a sort order setting region 56, and a search result display region 57 are included in the display screen 50.

The diagnostic image input from the diagnostic image input section 13 is displayed in the diagnostic image display region 51. As illustrated in FIG. 5 that illustrates an enlarged view of the diagnostic image display region 51, the entire diagnostic image is zoomed out and displayed at the lower right in the diagnostic image display region 51, and an zoom-in region 52 indicated in the entire diagnostic image represents a range that is zoomed in and displayed in the diagnostic image display region 51.

The user is allowed to arbitrarily scroll the diagnostic image displayed in the diagnostic image display region 51, to zoom in or out the diagnostic image to an arbitrary magnification, and to rotate the diagnostic image. An operation history at this time is recorded at predetermined sampling intervals to generate diagnosis-time image control information.

FIG. 6 illustrates an example of the diagnosis-time image control information. The diagnosis-time image control information 60 is configured of timings of sampling intervals, an X coordinate, a Y coordinate, and magnification.

For example, FIG. 6 indicates a case where the diagnostic image centering coordinates (330, 456) is displayed under a magnification of 10 at timings t1 and t2. Then, FIG. 6 indicates a case where, at a timing t3, the diagnostic image is scrolled to move a center thereof to coordinates (442, 463), and is zoomed in and displayed under a magnification of 20. Then, FIG. 6 indicates a case where, at a timing t4, the diagnostic image is further zoomed in and displayed under a magnification of 40.

Return to FIG. 4. As illustrated in FIG. 7 that illustrates an enlarged view of the diagnostic image display region 51, the query image set frame 53 is allowed to be provided on the diagnostic image displayed in the diagnostic image display region 51. The user is allowed to move the query image set frame 53 to an arbitrary position on the diagnostic image in the diagnostic image display region 51. The region indicated by the query image set frame 53 on the diagnostic image serves as a query image.

In the list number setting region 54, the user is allowed to set the number of systems (list number) of secondary filtering results obtained by further narrowing the primary filtering results. As with a case in FIG. 4, when the list number is set to 2, only two systems (55-1 and 55-2) of the keyword input region 55 are displayed. Moreover, two systems of search results are displayed in the search result display region 57.

In the keyword input region 55, the user is allowed to select or directly input a keyword as one item of research result filtering information for further narrowing the primary filtering results. The keyword selected or directly input serves as a search word for the chart information 45 of the case information 40. It is to be noted that, in a case in FIG. 3, a keyword in a case where the diagnostic image is a pathological image of a stomach is illustrated, and in the keyword input region 55-1, "Por" and "Sig" are selected as keywords. Moreover, in the keyword input region 55-5, "Non Cancer" is selected as a keyword.

In the sort order setting region 56, the user is allowed to set criteria when the secondary filtering results are sorted. In the case in FIG. 3, sort criteria in a case where the diagnostic image is a pathological image of the stomach are illustrated, and the sort criteria are set to "nucleus size".

It is to be noted that, in the keyword input region 55 and the sort order setting region 56, the user is allowed to change items thereof depending on a living body part appearing in the diagnostic image. FIG. 8A illustrates keywords and sort criteria in a case where the diagnostic image is a pathological image of a stomach. FIG. 8B illustrates keywords and sort criteria in a case where the diagnostic image is a pathological image of a prostate gland. It is to be noted that FIG. 8 illustrates only two examples in the cases where the diagnostic image is the pathological image of the stomach or prostate gland; however, as a matter of course, keywords and sort criteria corresponding to a case other than these cases may be prepared.

FIG. 9 illustrates items of secondary filtering information generated depending on setting of the keyword input region 55 and the sort order setting region 56.

The secondary filtering information 70 includes a filtering keyword 71, sort criteria 72, a similar image ID 73, and case image control information 74.

The filtering keyword 71 is a keyword selected or directly input in the keyword input region 55, and is a search word used to narrow the primary filtering results, based on the chart information 45 of the case information 40. The sort criteria 72 indicate criteria set in the sort order setting region 56. The similar image ID 73 is identification information of a search result (a similar image) to which the user refers in search results (similar images) displayed in the search result display region 57. The case image control information 74 is information representing an operation history when the similar image indicated by the similar image ID 73 is displayed for reference for the user.

Return to FIG. 4. In the search result display region 57, secondary filtering results based on the secondary filtering information including the keyword set or directly input in the keyword input region 55 are sorted according to the sort criteria set in the sort order setting region 56, and the sorted secondary filtering results are displayed.

FIG. 10 illustrates a display example in a case where the list number is set to 1 in the list number setting region 54, all keywords are selected in the keyword input region 55, and image feature amount similarity is set as sort criteria in the sort order setting region 56.

FIG. 11 illustrates a display example in a case where the list number is set to 2 in the list number setting region 54, all keywords except for "Not Cancer" are selected in the keyword input region 55-1, "Not Cancer" is selected in the keyword input region 55-2, and angle-of-view feature amount similarity is set as sort criteria in the sort order setting region 56. In this case, case images of various cancers similar to the diagnostic image and non-cancer case images are allowed to be displayed as search results.

FIG. 12 illustrates a display example in a case where the list number is set to 3 in the list number setting region 54, "Tub2", "Por", and "Sig" are selected in the keyword input regions 55-1, 55-2, and 55-3, respectively, and angle-of-view feature amount similarity is set as sort criteria in the sort order setting region 56. In this case, case images of respective suspected cases for the diagnostic image are allowed to be displayed in respective columns.

It is to be noted that a settable list number in the list number setting region 54 may be 4 or more.

[Description of Operation]

Next, an operation of the similar case image presentation unit 10 will be described below. FIG. 13 is a flow chart describing a similar case image presenting process by the similar case image presentation unit 10.

In step S1, the diagnostic image input section 13 determines a diagnostic image as a diagnostic target from prepared pathological images in response to an operation signal based on a selection operation by the user input from the operation input section 11 to input the diagnostic image to the display control section 12 and the query image setting section 14. The display control section 12 allows the diagnostic image to be displayed on the display. At this time, when the user scrolls or zooms in or out the diagnostic image, a history of such an operation is stored as diagnosis-time image control information.

In step S2, the query image setting section 14 extracts, as a query image, a region in the query image set frame 53 set by the user on the displayed diagnostic image, and inputs the query image to the case image obtaining section 15. The case image obtaining section 15 transmits the query image to the case search server 20 to request retrieval.

In step S3, the image feature amount extraction section 21 of the case search server 20 extracts the image feature amount from the query image to supply the image feature amount to the case image search section 22.

In step S4, the case image search section 22 retrieves a case image including a sub-image similar to the query image from the case database 23, based on the image feature amount of the query image. More specifically, similarity between the image feature amount of the query image and the image feature amount 44 of the case information 40 is calculated with use of, for example, the following expression (1). Then, a predetermined number of case images are detected in descending order of similarity, or case images with higher similarity than a predetermined threshold value are detected, and the case images are input to the first filter section 25 as search results.

[Math. 1]

$$S = \sum_{i=1}^{N} W_i(Q_i - D_i)^2 \quad (1)$$

Herein, N represents the number of dimensions of a feature amount, Q represents a feature amount of the query image, D represents a feature amount of an image in the case database, w represents weight parameters for respective feature dimensions. All of the weight parameters for the respective feature dimensions may be, for example, 1, or distance metric learning in a feature space relating to similarity may be performed by a known technique, and a value obtained by the learning may be applied to the weight parameters for the respective feature dimensions.

It is to be noted that a similarity calculation method is not limited to the expression (1), and any method may be used.

In step S5, the first filter section 25 performs primary filtering on each case information 40 retrieved as information similar in the image feature amount to the query image, based on the diagnosis-time image control information. More specifically, similarity between the diagnosis-time image control information of the diagnostic image and the diagnosis-time image control information 46 of each case information 40 (diagnosis-time image control information when the case image is diagnosed) is calculated. Then, a predetermined number of pieces of case information 40 are detected in descending order of similarity, or pieces of case information 40 with higher similarity than a predetermined threshold value are detected, and the pieces of the case information 40 are input to the second filter section 26 as primary filtering results.

An example of a similarity calculation method of the diagnosis-time image control information will be described below referring to FIG. 14. FIG. 14 describes a method of determining similarity by focusing attention on change in an X coordinate value of the diagnosis-time image control information.

First, time of the diagnosis-time image control information and a coordinate value of a pixel are converted into relative values. Herein, relative time to total time taken for diagnosis and relative coordinates obtained assuming that an image size is 1000 pixels are calculated. When relative coordinates obtained from the diagnosis-time image control information of the diagnostic image and the diagnosis-time image control information of the retrieved case image are plotted in graphs, these two graphs are as illustrated in FIG. 8, and similarity between these two graphs is calculated.

As a method of calculating similarity between the graphs, for example, an expression using the Bhattacharyya distance represented by the following expression (2) may be adopted, where diagnosis time is t, and the two graphs are p(t) and q(t).

[Math. 2]

$$S_x(p, q) = 1 - \sum_t \sqrt{p(t)q(t)} \quad (2)$$

It is to be noted that, in the above description, similarity is determined by focusing attention on change in the X coordinate value of the diagnosis-time image control information; however, attention may be focused on change in a Y coordinate value, change in display magnification, change in a movement difference value of the X coordinate value. In a case where the movement difference value is used, a range observed in diagnosis is found; therefore, it is expected to obtain a size value of a tumor.

It is to be noted that, in a case where a plurality of similarities are obtained by focusing attention on change in the X coordinate value, change in the Y coordinate value, and change in display magnification, each of the plurality of similarities may be subjected to threshold value processing, and the processed similarities may be used as results of filtering, or the plurality of similarities integrated with use of the following expression (3) may be used.

[Math. 3]

$$S_c = \alpha S_x + \beta S_y + \gamma S_m \quad (3)$$

In this expression, $S_x$, $S_y$, and $S_m$ are similarities focused on the X coordinate value, the Y coordinate value, and the display magnification of diagnosis-time image control information, respectively, and $\alpha$, $\beta$, and $\gamma$ are weight parameters for them. All of the weight parameters for respective feature dimensions may be, for example, 1, or distance metric learning in a feature space relating to similarity may be performed by a known technique, and a value obtained by the learning may be applied to the weight parameters for the respective feature dimensions.

After the primary filtering results are obtained in such a manner, processing proceeds to step S6 in FIG. 13. In the step S6, the second filter section 26 performs secondary filtering on the primary filtering results, based on secondary filtering information. More specifically, chart information 45 included in the case information 40 of the primary filtering results is retrieved with use of a keyword (a filtering keyword 71) set in the keyword input region 55 of the screen 50 as a search word to narrow the primary filtering results, or results narrowed by the keyword are sorted, based on sort criteria (sort criteria 72) set by the sort order setting region 56. Moreover, similarity between the case image control information 74 of the secondary filtering information 70 and the diagnosis-time image control information 46 of the primary filtering result may be calculated in a method similar to the primary filtering, and narrowing may be performed, based on the calculated similarity.

In step S7, the search result output section 27 outputs secondary filtering results (case images each of which includes a region serving as a similar image) by the second filter section 26 to the case image obtaining section 15 of the similar case image presentation unit 10. The case image obtaining section 15 supplies the case images as search results responded from the case search server 20 to the display control section 12. The display control section 12 displays a screen as a user interface including the case images as the research results on the display 30. More specifically, the screen 50 as illustrated in FIGS. 10 to 12 is displayed according to the setting number in the list number setting region 54 of the screen 50. Thus, description of the similar case image presenting process is completed.

[About Use of Screen Serving as User Interface]

For example, in a case where the user does not find a specific case name for the diagnostic image, as illustrated in FIG. 10, all keywords may be selected in the keyword input region 55-1. In this case, search results based on similarity of the image feature amount are displayed on the search result display region 57, based on sort criteria (the image feature amount similarity in a case in FIG. 10).

When the user selects one of the case images listed and displayed in the search result display region 57, as illustrated in FIG. 15, the display 40 displays a screen 60 in which the query image on the diagnostic image and the similar image on the selected case image are displayed side by side. Therefore, the user is allowed to closely compare the query image and the similar image that are zoomed in and displayed to each other.

For example, in a case where two systems of cancer case images and non-cancer case images are displayed as search results, as illustrated in FIG. 11, the list number is set to 2 in the list number setting region 54, and all keywords other than "Not Cancer" may be selected in the keyword input region 55-1, and "Not Cancer" may be selected in the keyword input region 55-2.

When the user selects one pathological image from each of two columns of case images listed and displayed in the search result display region 57 in FIG. 11, as illustrated in FIG. 16, the display 30 displays a screen in which the similar image on the selected cancer case image, the query image on the diagnostic image, and the similar image on the selected non-cancer case image are displayed side by side. Thus, the user is allowed to closely compare the query image that is zoomed in and displayed in a center of the screen to the cancer similar image and the non-cancer similar image that are zoomed in and displayed on both sides of the query image A primary purpose of pathological image diagnosis is mainly to determine whether or not a lesion is included in the diagnostic image; therefore, as illustrated in FIG. 11, it may be expected that displaying of a group of lesion (cancer) case images similar to the query image and a group of non-lesion (non-cancer) case images similar to the query image together with the query image is extremely useful in diagnosis. In other words, the user is allowed to easily diagnose whether the query image is similar to a group with a lesion or a group without lesion by comparison.

It is to be noted that, for example, in a case where the list number is set to 6 in the list number setting region 54, "Tub1", "Tub2", "Por", "Sig", "MUC", and "Not Cancer" are selected in the keyword input regions 55-1 to 55-6, respectively, and the user selects one pathological image from each of six columns of case images listed and displayed on the search result display region 57, a screen 80 illustrated in FIG. 16 in which similar images on the selected case images are displayed around the query image on the diagnostic image as a center is displayed. Thus, the user is allowed to closely compare the query image displayed in the center to a plurality of similar images displayed around the query image.

As illustrated in FIGS. 15 to 17, in a case where one of the query image and the similar image that are displayed side by side is scroll-displayed or zoomed in or out, the other of them is allowed to be also scroll-displayed or zoomed in or out accordingly.

It is to be noted that, in a case where one of the query image and the similar image is scroll-displayed or zoomed in or out, setting to keep the other of them as it is (not to scroll-display or zoom in or out the other of them) may be possible.

FIG. 18 illustrates a state in which, in a case where one of the query image and the similar image that are displayed side by side in the screen 60 illustrated in FIG. 15 is scroll-displayed, the other of them is also scroll-displayed accordingly. Comparison with a corresponding region is easily made by scroll-displaying one of the query image and the similar image and also scroll-displaying the other of them accordingly; therefore, this contributes to an improvement in diagnosis efficiency of the user.

FIG. 19 illustrates a state in which, in a case where one of the query image and the similar image that are displayed side by side in the screen 60 illustrated in FIG. 15 is zoomed in, the other of them is also zoomed in accordingly. Comparison with a corresponding region is easily made by zooming in or out one of the query image and the similar image and also zooming in or out the other of them accordingly; therefore, this contributes to an improvement in diagnosis efficiency of the user.

It is to be noted that FIG. 18 and FIG. 19 illustrate a case where one similar image is displayed for one query image; however, even in a case where two or more similar images are displayed for one query image, in response to scroll-displaying or zooming in or out of one image of the two or more similar images and the query image the other images of them may be also scroll-displayed or zoomed in or out accordingly.

FIG. 20 and FIG. 21 are diagrams for describing movement of a center point in a case where, in response to zooming in or out of one of the query image and the similar image, the other of them is also zoomed in or out accordingly.

It is to be noted that A in FIG. 20 illustrates a state in which the magnifications of the query image and the similar image are decreased to display the entire diagnostic image and the entire case image, B in FIG. 20 illustrates a state in which the query image and the similar image are displayed, and C in FIG. 20 illustrates a state in which the query image and the similar image are zoomed in and displayed. FIG. 21 illustrates movement of a center of a region that is to be zoomed in when one of the query image and the similar image is zoomed in and the other of them is also zoomed in.

For example, in a case where switching from the state illustrated in B in FIG. 20 to the state illustrated in A in FIG. 20 is performed, magnifications of the query image and the similar image are controlled to be decreased using, as center points, not centers of the query image and the similar image but centers of the diagnostic image including the query image and the case image including the similar image. On the contrary, in a case where switching from the state illustrated in A in FIG. 20 to the state illustrated in B in FIG. 20 is performed, as illustrated in FIG. 21, the magnifications of the query image and the similar image are controlled to be increased using, as center points, not the centers of the diagnostic image as a base of the query image and the case image as a base of the similar image but the centers of the query image and the similar image.

Moreover, for example, in a case where switching from the state illustrated in B in FIG. 20 to the state illustrated in C in FIG. 20 is performed, the magnifications of the query image and the similar image are controlled to be increased using, as center points, the centers of the query image and the similar image. On the contrary, in a case where switching from the state illustrated in C in FIG. 20 to the state illustrated in B in FIG. 20 is performed, the magnifications of the query image and the similar image are controlled to be decreased using, as center points, the centers of the query image and the similar image.

Thus, diagnosis efficiency by image comparison of the user is allowed to be improved by moving the center points in a case where, in response to zooming in or out of one of the query image and the similar image, the other of them is also zoomed in or out accordingly.

Incidentally, the above-described processes are allowed to be executed by hardware or software. In a case where the processes are executed by software, a program forming the software is installed into a computer. The computer used herein may include a computer mounted in dedicated hardware, and a general-purpose personal computer capable of executing various functions by installing various programs into the computer.

FIG. 22 is a block diagram illustrating a configuration example of hardware of a computer that executes the above-described processes with use of a program.

In such a computer 200, a CPU (Central Processing Unit) 201, a ROM (Read Only Memory) 202, and a RAM (Random Access Memory) 203 are connected to one another through a bus 204.

An input/output interface 205 is further connected to the bus 204. An input section 206, an output section 207, a storage section 208, a communication section 209, and a drive 210 are connected to the input/output interface 205.

The input section 206 may be configured of a keyboard, a mouse, a microphone, and the like. The output section 207 may be configured of a display, a speaker, and the like. The storage section 208 may be configured of a hard disk, a nonvolatile memory, and the like. The communication section 209 may be configured of a network interface and the like. The drive 210 may drive a removable medium 211 such as a magnetic disk, an optical disk, a magneto-optical disk, or a semiconductor memory.

In the computer 200 configured as described above, when the CPU 201 loads a program stored in the storage section 208 into the RAM 203 through the input/output interface 205 and the bus 204, and executes the program, the above-described processes are performed.

The program that is executed by the computer 200 (the CPU 201) may be provided as a so-called web application that is allowed to be obtained and executed by accessing a predetermined server on the Internet.

Moreover, the program is allowed to be installed into the storage section 208 through the input/output interface 205 by mounting the removable medium 211 into the drive 210. Further, the program is allowed to be received by the communication section 209 through a wired or wireless transmission medium, and then be installed into the storage section 208. In addition, the program is allowed to be installed into the ROM 202 or the storage section 208 in advance.

It is to be noted that the program that is executed by the computer 200 may be a program in which processes are performed time-sequentially in the order described in the description or a program in which processes are performed concurrently or at a necessary timing such as when a call is made.

It is to be noted that the embodiments of the present disclosure are not limited to the above-described embodiments, and various modifications are possible without departing from the scope of the present disclosure.

It should be understood by those skilled in the art that various modifications, combinations, sub-combinations, and alterations may occur depending on design requirements and other factors insofar as they are within the scope of the appended claims or the equivalents thereof.

The invention claimed is:

1. An information processing system comprising:
a diagnostic image acquisition section configured to acquire a diagnostic image;

a communication section configured to
transmit a search request to a diagnosed image search unit, wherein the search request is a request to search for a similar diagnosed image based on a predetermined region of the diagnostic image and information related to the diagnostic image, and
receive the similar diagnosed image in response to the search request; and
a display control section configured to cause a display device to display the predetermined region of the diagnostic image and the similar diagnosed image,
wherein the information related to the diagnostic image is based on operation history information related to display of the diagnostic image, the operation history information including one or more operations performed by a user with respect to the display of the diagnostic image.

2. The information processing system according to claim 1, wherein the operation history information includes at least one of movement, enlargement, reduction, or rotation of the diagnostic image.

3. The information processing system according to claim 1, wherein the display control section causes the display device to display the predetermined region of the diagnostic image and the similar diagnosed image side by side.

4. The information processing system according to claim 1, wherein, when the display control section causes the display device to display the predetermined region of the diagnostic image and the similar diagnosed image for comparison, in response to an operation from the user to instruct movement or zooming in or out or rotating of one of the diagnostic image and the similar diagnosed image, the display control section also moves or zooms in or out or rotates the other one of the diagnostic image and the similar diagnosed image.

5. The information processing system according to claim 1, wherein the diagnostic image and the similar diagnosed image are medical images.

6. The information processing system according to claim 1, wherein the diagnostic image and the similar diagnosed image are pathological images obtained by scanning a prepared specimen, the prepared specimen being formed by placing, on a glass slide, a biopsy specimen cut from a pathological tissue.

7. The information processing system according to claim 1, wherein the diagnosed image search unit is a server provided on the Internet.

8. The information processing system according to claim 1, wherein the display control section causes the display device to display, as the similar diagnosed images, one or more first case images associated with information that a predetermined lesion is present and one or more second case images associated with information that the lesion is not present.

9. The information processing system according to claim 8, wherein the display control section causes the display device to display, in association with the one or more first case images, display information indicating that the lesion is present, and, in association with the one or more second case images, display information indicating that the lesion is not present.

10. The information processing system according to claim 1, wherein the predetermined region of the diagnostic image and the similar diagnosed image are displayed in a comparative manner.

11. The information processing system according to claim 1, wherein the communication section receives the similar diagnosed image according to similarity between the operation history information of the diagnostic image and operation history information of the similar diagnosed image.

12. An information processing method comprising:
acquiring a diagnostic image;
transmitting a request to search for a similar diagnosed image based on a predetermined region of the diagnostic image and information related to the diagnostic image;
receiving the similar diagnosed image in response to the search request; and
displaying, on a display device, the predetermined region of the diagnostic image and the similar diagnosed image,
wherein the information related to the diagnostic image is based on operation history information related to display of the diagnostic image, the operation history information including one or more operations performed by a user with respect to the display of the diagnostic image.

13. The information processing method according to claim 12, wherein the similar diagnosed image is received according to similarity between the operation history information of the diagnostic image and operation history information of the similar diagnosed image.

14. The information processing method according to claim 12, wherein the operation history information includes at least one of movement, enlargement, reduction, or rotation of the diagnostic image.

15. The information processing method according to claim 12, wherein the predetermined region of the diagnostic image and the similar diagnosed image are displayed side by side.

16. The information processing method according to claim 12, wherein, when the predetermined region of the diagnostic image and the similar diagnosed image are displayed for comparison, in response to an operation from the user to instruct movement or zooming in or out or rotating of one of the diagnostic image and the similar diagnosed image, the displaying of the other one of the diagnostic image and the similar diagnosed image also moves or zooms in or out or rotates.

17. The information processing method according to claim 12, wherein the diagnostic image and the similar diagnosed image are medical images.

18. The information processing method according to claim 12, wherein the diagnostic image and the similar diagnosed image are pathological images obtained by scanning a prepared specimen, the prepared specimen being formed by placing, on a glass slide, a biopsy specimen cut from a pathological tissue.

19. The information processing method according to claim 12, wherein the search request is transmitted to a server provided on the Internet.

20. The information processing method according to claim 12, wherein the display device displays, as the similar diagnosed images, one or more first case images associated with information that a predetermined lesion is present and one or more second case images associated with information that the lesion is not present.

21. The information processing method according to claim 20, wherein the display device displays, in association with the one or more first case images, display information indicating that the lesion is present, and, in association with the one or more second case images, display information indicating that the lesion is not present.

22. The information processing method according to claim 12, wherein the predetermined region of the diagnostic image and the similar diagnosed image are displayed in a comparative manner.

23. A non-transitory computer-readable medium having embodied thereon a program, which when executed by a computer causes the computer to execute a method, the method comprising:
   acquiring a diagnostic image;
   transmitting a request to search for a similar diagnosed image based on a predetermined region of the diagnostic image and information related to the diagnostic image;
   receiving the similar diagnosed image in response to the search request; and
   displaying, on a display device, the predetermined region of the diagnostic image and the similar diagnosed image,
   wherein the information related to the diagnostic image is based on operation history information related to display of the diagnostic image, the operation history information including one or more operations performed by a user with respect to the display of the diagnostic image.

24. The non-transitory computer-readable medium according to claim 23, wherein the similar diagnosed image is received according to similarity between the operation history information of the diagnostic image and operation history information of the similar diagnosed image.

25. The non-transitory computer-readable medium according to claim 23, wherein the operation history information includes at least one of movement, enlargement, reduction, or rotation of the diagnostic image.

26. The non-transitory computer-readable medium according to claim 23, wherein the predetermined region of the diagnostic image and the similar diagnosed image are displayed side by side.

27. The non-transitory computer-readable medium according to claim 23, wherein, when the predetermined region of the diagnostic image and the similar diagnosed image are displayed for comparison, in response to an operation from the user to instruct movement or zooming in or out or rotating of one of the diagnostic image and the similar diagnosed image, the displaying of the other one of the diagnostic image and the similar diagnosed image also moves or zooms in or out or rotates.

28. The non-transitory computer-readable medium according to claim 23, wherein the diagnostic image and the similar diagnosed image are medical images.

29. The non-transitory computer-readable medium according to claim 23, wherein the diagnostic image and the similar diagnosed image are pathological images obtained by scanning a prepared specimen, the prepared specimen being formed by placing, on a glass slide, a biopsy specimen cut from a pathological tissue.

30. The non-transitory computer-readable medium according to claim 23, wherein the search request is transmitted to a server provided on the Internet.

31. The non-transitory computer-readable medium according to claim 23, wherein the display device displays, as the similar diagnosed images, one or more first case images associated with information that a predetermined lesion is present and one or more second case images associated with information that the lesion is not present.

32. The non-transitory computer-readable medium according to claim 31, wherein the display device displays, in association with the one or more first case images, display information indicating that the lesion is present, and, in association with the one or more second case images, display information indicating that the lesion is not present.

33. The non-transitory computer-readable medium according to claim 23, wherein the predetermined region of the diagnostic image and the similar diagnosed image are displayed in a comparative manner.

34. An information processing system comprising:
   an image acquisition section configured to acquire a first image;
   a communication section configured to
      transmit a search request to an image search unit, wherein the search request is a request to search for a second image based on a predetermined region of the first image and information related to the first image, and
      receive the second image in response to the search request; and
   a display control section configured to cause a display device to display the predetermined region of the first image and the second image,
   wherein the information related to the first image is based on operation history information of the first image, the operation history information including one or more operations performed by a user with respect to the first image.

35. The information processing system according to claim 34, wherein the first image includes at least one of an image by CT, MRI, X-rays, or pathological image.

36. The information processing system according to claim 34, wherein the operation history information includes at least one of movement, enlargement, reduction, or rotation of the first image.

37. The information processing system according to claim 34, wherein the display control section causes the display device to display the predetermined region of the first and the second image side by side.

38. The information processing system according to claim 34, wherein, when the display control section causes the display device to display the predetermined region of the first image and the second image for comparison, in response to an operation from the user to instruct movement or zooming in or out or rotating of one of the first image and the second image, the display control section also moves or zooms in or out or rotates the other one of the first image and the second image.

39. The information processing system according to claim 34, wherein the first image and the second image are medical images.

40. The information processing system according to claim 34, wherein the first image and the second image are pathological images obtained by scanning a prepared specimen, the prepared specimen being formed by placing, on a glass slide, a biopsy specimen cut from a pathological tissue.

41. The information processing system according to claim 34, wherein the image search unit is a server provided on the Internet.

42. The information processing system according to claim 34, wherein the display control section causes the display device to display, as the second image, at least one first case image associated with information that a predetermined lesion is present and at least one second case image associated with information that the lesion is not present.

43. The information processing system according to claim 42, wherein the display control section causes the display device to display, in association with the at least one first case image, display information indicating that the lesion is present, and, in association with the at least one second case image, display information indicating that the lesion is not present.

44. The information processing system according to claim 34, wherein the predetermined region of the first image and the second image are displayed in a comparative manner.

* * * * *